(12) United States Patent
Köhn et al.

(10) Patent No.: US 9,332,759 B2
(45) Date of Patent: *May 10, 2016

(54) HERBICIDE SAFENER COMPOSITIONS

(75) Inventors: Arnim Köhn, Klein-Winterheim (DE);
Andreas Van Almsick, Karben (DE);
Hartmut Ahrens, Egelsbach (DE);
Frank Ziemer, Kriftel (DE); Simon Dörner-Rieping, Neu-Anspach (DE);
Christopher Hugh Rosinger, Hofheim (DE); Erwin Hacker, Langenenslingen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 169 days.

This patent is subject to a terminal disclaimer.

(21) Appl. No.: 14/004,868

(22) PCT Filed: Mar. 12, 2012

(86) PCT No.: PCT/EP2012/054286
§ 371 (c)(1),
(2), (4) Date: Dec. 23, 2013

(87) PCT Pub. No.: WO2012/123420
PCT Pub. Date: Sep. 20, 2012

(65) Prior Publication Data
US 2014/0121104 A1    May 1, 2014

(30) Foreign Application Priority Data

Mar. 15, 2011   (EP) .................................. 11158261

(51) Int. Cl.
| | |
|---|---|
| *A01N 43/82* | (2006.01) |
| *C07D 271/08* | (2006.01) |
| *C07D 413/12* | (2006.01) |
| *C07D 413/14* | (2006.01) |
| *C07D 417/14* | (2006.01) |

(52) U.S. Cl.
CPC .............. *A01N 43/82* (2013.01); *C07D 271/08* (2013.01); *C07D 413/12* (2013.01); *C07D 413/14* (2013.01); *C07D 417/14* (2013.01)

(58) Field of Classification Search
CPC ......................... A01N 43/82; A01N 2300/00
See application file for complete search history.

(56) References Cited

U.S. PATENT DOCUMENTS

| | | | | |
|---|---|---|---|---|
| 4,671,818 | A * | 6/1987 | Calvino et al. ................. | 504/265 |
| 8,288,316 | B2 | 10/2012 | Koehn et al. | |
| 9,035,064 | B2 * | 5/2015 | Kohn ..................... | A01N 43/82 504/103 |
| 2007/0021303 | A1 | 1/2007 | Risinger et al. | |
| 2011/0152084 | A1 | 6/2011 | Koehn et al. | |
| 2014/0309115 | A1 * | 10/2014 | Kraus .................... | A01N 43/82 504/239 |

FOREIGN PATENT DOCUMENTS

| | | |
|---|---|---|
| DE | 102004035136 | 2/2006 |
| EP | 0173657 | 3/1986 |
| WO | 2011035874 | 3/2011 |

OTHER PUBLICATIONS

International Search Report for PCT/EP2012/054286 Mailed May 23, 2012.

* cited by examiner

*Primary Examiner* — John Pak
*Assistant Examiner* — Nathan W Schlientz
(74) *Attorney, Agent, or Firm* — MMWV IP, LLC.

(57) ABSTRACT

Herbicide-safener compositions are described, comprising active ingredients from the group of the N-(1,2,5-oxadiazol-3-yl)benzamides and safeners. These herbicidal compositions are particularly suitable for use against harmful plants in crops of useful plants.

9 Claims, No Drawings

HERBICIDE SAFENER COMPOSITIONS

CROSS REFERENCE TO RELATED APPLICATIONS

This application is a §371 National Stage Application of PCT/EP2012/054286, filed Mar. 12, 2012, which claims priority to European Application No. 11158261.2, filed Mar. 15, 2011.

BACKGROUND OF THE INVENTION

1. Field of the Invention

The present invention relates to agrochemically active herbicide-safener compositions, to processes for production thereof and to the use thereof for control of harmful plants.

2. Description of Related Art

Various documents disclose that particular N-(1,2,5-oxadiazol-3-yl)benzamides have herbicidal properties. For instance, EP 0 173 657 A1 and WO 2011/035874 A1 describe such N-(1,2,5-oxadiazol-3-yl)benzamides, which control a broad spectrum of weeds. However, not all of these active ingredients are fully compatible with some important crop plants, such as cereal species, corn or rice. They cannot therefore be used in some crops in such a way that the desired broad herbicidal efficacy toward harmful plants is ensured.

SUMMARY

It is therefore an object of the present invention to provide herbicidal compositions in which the selectivity of the above-mentioned herbicides with respect to important crop plants is increased. This object is achieved by the inventive compositions, described hereinafter, comprising herbicides and safeners.

The present invention provides compositions comprising (A) one or more compounds of the formula (I) or salts thereof

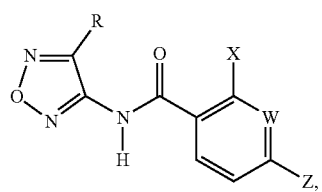

(I)

in which the symbols and indices are each defined as follows:

W is N or CY,

R is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, $(C_2-C_6)$-haloalkenyl, $(C_2-C_6)$-alkynyl, $(C_2-C_6)$-alkynyloxy, $(C_2-C_6)$-haloalkynyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl each substituted by s radicals from the group of methyl, ethyl, methoxy, trifluoromethyl and halogen, X and Z are each independently nitro, halogen, cyano, formyl, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, or heteroaryl, heterocyclyl or phenyl each substituted by s radicals from the group of methyl, ethyl, methoxy, nitro, trifluoromethyl and halogen, Y is hydrogen, nitro, halogen, cyano, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $CO_2R^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkylheteroaryl, $O—(C_1-C_6)$-alkylheterocyclyl, $O—(C_1-C_6)$-alkylheteroaryl, $(C_1-C_6)$-alkylheterocyclyl, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR^1R^2$, $P(O)(OR^5)_2$, tetrahydrofuranyloxymethyl, tetrahydrofuranylmethoxymethyl, $O(CH_2)$-3,5-dimethyl-1,2-oxazol-4-yl, $O(CH_2)_2$—O (3,5-dimethoxypyrimidin-2-yl, $O(CH_2)$-5-pyrrolidin-2-one, $O(CH_2)$-5-2,4-dimethyl-2,4-dihydro-3H-1,2,4-triazol-3-one, or heteroaryl or heterocyclyl each substituted by s radicals from the group of methyl, ethyl, methoxy, halogen and cyanomethyl, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl or phenyl-$(C_1-C_6)$-alkyl, where the 12 latter radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^3$, $NR^3COR^3$, $CO_2R^3$, $COSR^3$, $CON(R^3)_2$ and $(C_1-C_4)$-alkoxy-$(C_2-C_6)$-alkoxycarbonyl, $R^2$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, phenyl or phenyl-$(C_1-C_6)$-alkyl, where the seven latter radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^3$, $NR^3COR^3$, $CO_2R^3$, $COSR^3$, $CON(R^3)_2$ and $(C_1-C_4)$-alkoxy-$(C_2-C_6)$-alkoxycarbonyl, $R^3$ is hydrogen, $(C_1-C_6)$-alkyl, $(C_2-C_6)$-alkenyl or $(C_2-C_6)$-alkynyl, $R^4$ is $(C_1-C_6)$-alkyl, $(C_2-C_6)$-alkenyl or $(C_2-C_6)$-alkynyl, $R^5$ is methyl or ethyl, n is 0, 1 or 2, s is 0, 1, 2 or 3, and (B) one or more safeners.

DETAILED DESCRIPTION OF A PREFERRED EMBODIMENT

The inventive herbicide-safener combinations may comprise or be used together with additional further components, for example other kinds of active crop protection ingredients and/or additives and/or formulation auxiliaries customary in crop protection.

The herbicides (A) and the safeners (B) can be applied in a known manner, for example together (for example as a co-formulation or as a tank-mix) or else at different times (splitting), for example to the plants, plant parts, plant seeds or the area on which the plants grow. It is possible, for example, to apply the individual active ingredients or the herbicide-safener combination in several portions (sequential application), for example pre-emergence applications followed by post-emergence applications, or early post-emergence applications followed by post-emergence applications at an intermediate or late stage. Preference is given to the joint or immediately successive application of the active ingredients in the respective combination. It is also possible to use the individual active ingredients or the herbicide-safener combination for seed treatment.

Preference is given to those inventive compositions which comprise, as herbicide (A), compounds of the general formula (I) and salts thereof in which the symbols and indices are each defined as follows:

W is CY,
R is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, acetylamino, benzoylamino, methoxycarbonyl, ethoxycarbonyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl,
X and Z are each independently nitro, halogen, cyano, $(C_1-C_6)$-alkyl, $(C_1-C_6)$-haloalkyl, $(C_3-C_6)$-cycloalkyl, $OR^1$, $S(O)_n R^2$, $(C_1-C_6)$-alkyl-$S(O)_n R^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$ or 1,2,4-triazol-1-yl,
Y is hydrogen, nitro, halogen, cyano, $(C_1-C_6)$-alkyl, $(C_1-C_6)$-haloalkyl, $OR^1$, $S(O)_n R^2$, $SO_2N(R^1)_2$, $NR^1SO_2R^2$, $NR^1COR^1$, $(C_1-C_6)$-alkyl-$S(O)_n R^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, tetrahydrofuranyloxymethyl, tetrahydrofuranylmethoxymethyl, $O(CH_2)$-3,5-dimethyl-1,2-oxazol-4-yl, $O(CH_2)_2$—$O$(3,5-dimethoxypyrimidin-2-yl, $O(CH_2)$-5-pyrrolidin-2-one or $O(CH_2)$-5-2,4-dimethyl-2,4-dihydro-3H-1,2,4-triazol-3-one,
$R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, phenyl or phenyl-$(C_1-C_6)$-alkyl, where the seven latter radicals are substituted by s radicals from the group consisting of halogen and $OR^3$,
$R^2$ is $(C_1-C_6)$-alkyl, $(C_3-C_6)$-cycloalkyl or $(C_3-C_6)$-cycloalkyl-$(C_1-C_6)$-alkyl, where the three latter radicals are substituted by s radicals from the group consisting of halogen and $OR^3$,
$R^3$ is hydrogen or $(C_1-C_6)$-alkyl,
n is 0, 1 or 2,
s is 0, 1, 2 or 3.

Preference is also given to those inventive compositions which comprise, as herbicide (A), compounds of the general formula (I) and salts thereof in which the symbols and indices are each defined as follows:

W is N,
R is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, acetylamino, benzoylamino, methoxycarbonyl, ethoxycarbonyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl,
X and Z are each independently nitro, halogen, cyano, $(C_1-C_6)$-alkyl, $(C_1-C_6)$-haloalkyl, $(C_3-C_6)$-cycloalkyl, $OR^1$, $S(O)_n R^2$, $(C_1-C_6)$-alkyl-$S(O)_n R^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$ or 1,2,4-triazol-1-yl,
$R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, phenyl or phenyl-$(C_1-C_6)$-alkyl, where the seven latter radicals are substituted by s radicals from the group consisting of halogen and $OR^3$,
$R^2$ is $(C_1-C_6)$-alkyl, $(C_3-C_6)$-cycloalkyl or $(C_3-C_6)$-cycloalkyl-$(C_1-C_6)$-alkyl, where the three latter radicals are substituted by s radicals from the group consisting of halogen and $OR^3$,
$R^3$ is hydrogen or $(C_1-C_6)$-alkyl,
n is 0, 1 or 2,
s is 0, 1, 2 or 3.

Particular preference is given to those inventive compositions which comprise, as herbicide (A), compounds of the general formula (I) and salts thereof in which the symbols and indices are each defined as follows:

W is CY,
R is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, acetylamino, benzoylamino, methoxycarbonyl, ethoxycarbonyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl,
X and Z are each independently nitro, halogen, cyano, $(C_1-C_6)$-alkyl, $(C_1-C_6)$-haloalkyl, $(C_3-C_6)$-cycloalkyl, $OR^1$, $S(O)_n R^2$, $(C_1-C_6)$-alkyl-$S(O)_n R^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$ or 1,2,4-triazol-1-yl,
Y is nitro, halogen, cyano, $(C_1-C_6)$-alkyl, $(C_1-C_6)$-haloalkyl, $OR^1$, $S(O)_n R^2$, $SO_2N(R^1)_2$, $NR^1SO_2R^2$, $NR^1COR^1$, $(C_1-C_6)$-alkyl-$S(O)_n R^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, tetrahydrofuranyloxymethyl, tetrahydrofuranylmethoxymethyl, $O(CH_2)$-3,5-dimethyl-1,2-oxazol-4-yl, $O(CH_2)_2$—$O$-((3,5-dimethoxypyrimidin)-2-yl, $O(CH_2)$-5-pyrrolidin-2-one or $O(CH_2)$-5-2,4-dimethyl-2,4-dihydro-3H-1,2,4-triazol-3-one,
$R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, phenyl or phenyl-$(C_1-C_6)$-alkyl, where the seven latter radicals are substituted by s radicals from the group consisting of halogen and $OR^3$,
$R^2$ is $(C_1-C_6)$-alkyl, $(C_3-C_6)$-cycloalkyl or $(C_3-C_6)$-cycloalkyl-$(C_1-C_6)$-alkyl, where the three latter radicals are substituted by s radicals from the group consisting of halogen and $OR^3$,
$R^3$ is hydrogen or $(C_1-C_6)$-alkyl,
n is 0, 1 or 2,
s is 0, 1, 2 or 3.

Very particular preference is given to those inventive compositions which comprise, as herbicide (A), compounds of the general formula (I) and salts thereof in which the symbols and indices are each defined as follows:

W is CY,
R is amino, cyclopropyl, isopropyl, n-propyl, methyl, ethyl, methoxy, bromine, chlorine or fluorine,
X is chlorine, trifluoromethyl or methyl,
Y is $CH_2OCH_2CF_3$, $SO_2Me$, $S(O)Me$ or $SMe$,
Z is trifluoromethyl, $SO_2Me$, $S(O)Me$ or $SMe$.

Very particular preference is also given to those inventive compositions which comprise, as herbicide (A), compounds of the general formula (I) and salts thereof in which the symbols and indices are each defined as follows:
W is N,
R is amino, cyclopropyl, isopropyl, t-butyl, methyl, ethyl, methoxy, bromine or chlorine,
X is chlorine, methoxymethyl or methyl,
Z is trifluoromethyl.

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. Halogen is fluorine, chlorine, bromine or iodine.

Heterocyclyl is a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl, Heteroaryl is an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned.

The present invention also provides herbicide-safener compositions comprising stereoisomers and mixtures thereof which are encompassed by the formula (I) or by the formulae of component B (safeners). Such compounds of the formula (I) or of the formulae of component B (safeners) contain, for example, one or more asymmetrically substituted carbon atoms or sulfoxides. The possible stereoisomers defined by the specific three-dimensional shape thereof, such as enantiomers and diastereomers, are all encompassed by the formula (I) or by the formulae of component B (safeners); especially also the racemic mixtures and—where enantiomers are possible—both enantiomers and especially the respective biologically active enantiomer. The individual stereoisomers can be obtained by customary methods from mixtures of the stereoisomers or else by stereoselective reactions in combination with the use of stereochemically pure starting materials or auxiliaries.

In the case of radicals with carbon atoms, preference is given in principle to those having 1 to 6 carbon atoms, preferably 1 to 4 carbon atoms, especially 1 or 2 carbon atoms.

Examples of compounds used as herbicide (A) are listed in the following tables:
In these tables, the abbreviations used mean:

| Et = ethyl | Me = methyl | n-Pr = n-propyl | i-Pr = isopropyl |
| c-Pr = cyclopropyl | Ph = phenyl | Ac = acetyl | t-Bu = tert-butyl |

TABLE 1

Inventive compounds of the general formula (I) in which A is CY

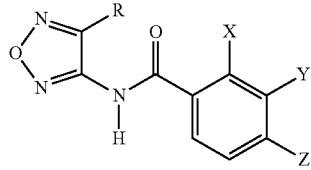

| Ex. No | R | X | Y | Z |
|---|---|---|---|---|
| A1-1 | NH$_2$ | Cl | CH$_2$OCH$_2$CF$_3$ | SO$_2$Me |
| A1-2 | c-Pr | Cl | CH$_2$OCH$_2$CF$_3$ | SO$_2$Me |
| A1-3 | i-Pr | Cl | CH$_2$OCH$_2$CF$_3$ | SO$_2$Me |
| A1-4 | Me | Cl | CH$_2$OCH$_2$CF$_3$ | SO$_2$Me |
| A1-5 | n-Pr | Cl | CH$_2$OCH$_2$CF$_3$ | SO$_2$Me |
| A1-6 | Et | Cl | CH$_2$OCH$_2$CF$_3$ | SO$_2$Me |
| A1-7 | 1,2,4-triazol-1-yl | Cl | CH$_2$OCH$_2$CF$_3$ | SO$_2$Me |
| A1-8 | Ph | Cl | CH$_2$OCH$_2$CF$_3$ | SO$_2$Me |
| A1-9 | CN | Cl | CH$_2$OCH$_2$CF$_3$ | SO$_2$Me |
| A1-10 | thiophen-2-yl | Cl | CH$_2$OCH$_2$CF$_3$ | SO$_2$Me |
| A1-11 | OMe | Cl | CH$_2$OCH$_2$CF$_3$ | SO$_2$Me |
| A1-12 | n-Pr | Cl | CH$_2$OCH$_2$CF$_3$ | SO$_2$Me |
| A1-13 | Br | Cl | CH$_2$OCH$_2$CF$_3$ | SO$_2$Me |
| A1-14 | Cl | Cl | CH$_2$OCH$_2$CF$_3$ | SO$_2$Me |
| A1-15 | F | Cl | CH$_2$OCH$_2$CF$_3$ | SO$_2$Me |
| A1-16 | 4-F-phenyl | Cl | CH$_2$OCH$_2$CF$_3$ | SO$_2$Me |
| A1-17 | t-Bu | Cl | CH$_2$OCH$_2$CF$_3$ | SO$_2$Me |
| A1-18 | NO$_2$ | Cl | CH$_2$OCH$_2$CF$_3$ | SO$_2$Me |
| A1-19 | NH$_2$ | Cl | 5-cyanomethyl-4,5-dihydro-1,2-oxazol-3-yl | SO$_2$Et |
| A1-20 | n-Pr | Cl | 5-cyanomethyl-4,5-dihydro-1,2-oxazol-3-yl | SO$_2$Et |
| A1-21 | t-Bu | Cl | 5-cyanomethyl-4,5-dihydro-1,2-oxazol-3-yl | SO$_2$Et |
| A1-22 | Et | Cl | 5-cyanomethyl-4,5-dihydro-1,2-oxazol-3-yl | SO$_2$Et |
| A1-23 | c-Pr | Cl | 5-cyanomethyl-4,5-dihydro-1,2-oxazol-3-yl | SO$_2$Et |
| A1-24 | Me | Cl | 5-cyanomethyl-4,5-dihydro-1,2-oxazol-3-yl | SO$_2$Et |
| A1-25 | NO$_2$ | Cl | 5-cyanomethyl-4,5-dihydro-1,2-oxazol-3-yl | SO$_2$Et |
| A1-26 | 4-F-phenyl | Cl | 5-cyanomethyl-4,5-dihydro-1,2-oxazol-3-yl | SO$_2$Et |
| A1-27 | 1,2,4-triazol-1-yl | Cl | 5-cyanomethyl-4,5-dihydro-1,2-oxazol-3-yl | SO$_2$Et |
| A1-28 | CN | Cl | 5-cyanomethyl-4,5-dihydro-1,2-oxazol-3-yl | SO$_2$Et |
| A1-29 | i-Pr | Cl | 5-cyanomethyl-4,5-dihydro-1,2-oxazol-3-yl | SO$_2$Et |
| A1-30 | OMe | Cl | 5-cyanomethyl-4,5-dihydro-1,2-oxazol-3-yl | SO$_2$Et |
| A1-31 | Cl | Cl | 5-cyanomethyl-4,5-dihydro-1,2-oxazol-3-yl | SO$_2$Et |
| A1-32 | Br | Cl | 5-cyanomethyl-4,5-dihydro-1,2-oxazol-3-yl | SO$_2$Et |
| A1-33 | Me | Cl | 5-methoxymethyl-4,5-dihydro-1,2-oxazol-3-yl | SO$_2$Et |
| A1-34 | Me | CF$_3$ | SEt | SO$_2$Me |
| A1-35 | Me | CF$_3$ | S(O)Et | SO$_2$Me |
| A1-36 | Me | CF$_3$ | SO$_2$Me | SO$_2$Me |
| A1-37 | Me | CF$_3$ | OCH$_2$CH$_2$OMe | SO$_2$Me |
| A1-38 | Me | CF$_3$ | SMe | SO$_2$Me |
| A1-39 | Me | CF$_3$ | O—CH$_2$-tetrahydrofuran-2-yl | SO$_2$Et |
| A1-40 | NHAc | Me | SO$_2$Me | CF$_3$ |
| A1-41 | NH$_2$ | Me | SO$_2$Me | CF$_3$ |
| A1-42 | OMe | Me | SO$_2$Me | CF$_3$ |
| A1-43 | Et | Me | SO$_2$Me | CF$_3$ |
| A1-44 | Me | Me | SO$_2$Me | CF$_3$ |
| A1-45 | Cl | Me | SO$_2$Me | CF$_3$ |
| A1-46 | Br | Me | SO$_2$Me | CF$_3$ |
| A1-47 | NO$_2$ | Me | SO$_2$Me | CF$_3$ |
| A1-48 | 1,2,4-triazol-1-yl | Me | SO$_2$Me | CF$_3$ |
| A1-49 | CH$_2$OMe | Me | SO$_2$Me | CF$_3$ |
| A1-50 | SMe | Me | SO$_2$Me | CF$_3$ |
| A1-51 | i-Pr | Me | SO$_2$Me | CF$_3$ |

TABLE 1-continued

Inventive compounds of the general formula (I) in which A is CY

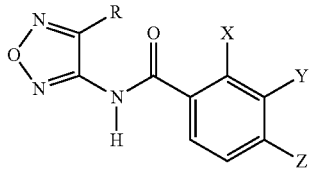

| Ex. No | R | X | Y | Z |
|---|---|---|---|---|
| A1-52 | t-Bu | Me | SO$_2$Me | CF$_3$ |
| A1-53 | c-Pr | Me | SO$_2$Me | CF$_3$ |
| A1-54 | n-Pr | Me | SO$_2$Me | CF$_3$ |
| A1-55 | F | Me | SO$_2$Me | CF$_3$ |
| A1-56 | Me | Me | SO$_2$-cyclopentyl | CF$_3$ |
| A1-57 | Me | Me | SO$_2$Me | CF$_2$CF$_3$ |
| A1-58 | Me | Me | SO$_2$CH$_2$CH=CHCH$_3$ | CF$_3$ |
| A1-59 | Me | Et | SO$_2$Me | CF$_3$ |
| A1-60 | Me | Me | SO$_2$Et | CF$_3$ |
| A1-61 | Me | Me | S(O)Et | CF$_3$ |
| A1-62 | Me | Me | SO$_2$Me | SO$_2$Me |
| A1-63 | Et | Me | SO$_2$Me | SO$_2$Me |
| A1-64 | n-Pr | Me | SO$_2$Me | SO$_2$Me |
| A1-65 | i-Pr | Me | SO$_2$Me | SO$_2$Me |
| A1-66 | NHAc | Me | SO$_2$Me | SO$_2$Me |
| A1-67 | c-Pr | Me | SO$_2$Me | SO$_2$Me |
| A1-68 | Cl | Me | SO$_2$Me | SO$_2$Me |
| A1-69 | Br | Me | SO$_2$Me | SO$_2$Me |
| A1-70 | 1,2,4-triazol-1-yl | Me | SO$_2$Me | SO$_2$Me |
| A1-71 | NH$_2$ | Me | SO$_2$Me | SO$_2$Me |
| A1-72 | Me | Me | SO$_2$Et | SO$_2$Me |
| A1-73 | Me | Me | SEt | SO$_2$Me |
| A1-74 | t-Bu | Me | S(O)Me | CF$_3$ |
| A1-75 | Et | Me | S(O)Me | CF$_3$ |
| A1-76 | n-Pr | Me | S(O)Me | CF$_3$ |
| A1-77 | i-Pr | Me | S(O)Me | CF$_3$ |
| A1-78 | c-Pr | Me | S(O)Me | CF$_3$ |
| A1-79 | NO$_2$ | Me | S(O)Me | CF$_3$ |
| A1-80 | OMe | Me | S(O)Me | CF$_3$ |
| A1-81 | F | Me | S(O)Me | CF$_3$ |
| A1-82 | Cl | Me | S(O)Me | CF$_3$ |
| A1-83 | Br | Me | S(O)Me | CF$_3$ |
| A1-84 | 1,2,4-triazol-1-yl | Me | S(O)Me | CF$_3$ |
| A1-85 | Me | Me | S(O)Me | CF$_3$ |
| A1-86 | Me | F | S(O)Me | CF$_3$ |
| A1-87 | Me | Me | S(O)Et | CF$_3$ |
| A1-88 | Me | OMe | SO$_2$Et | CF$_3$ |
| A1-89 | Me | Me | SO$_2$CH$_2$CH$_2$OMe | SO$_2$Me |
| A1-90 | Me | Me | S(O)CH$_2$CH$_2$OMe | SO$_2$Me |
| A1-91 | Me | Me | SO$_2$CH$_2$CH$_2$OMe | CF3 |
| A1-92 | Me | Cl | pyrazol-1-yl | SO$_2$Me |
| A1-93 | Et | Cl | pyrazol-1-yl | SO$_2$Me |
| A1-94 | OMe | Cl | pyrazol-1-yl | SO$_2$Me |
| A1-95 | Cl | Cl | pyrazol-1-yl | SO$_2$Me |
| A1-96 | Me | Me | pyrazol-1-yl | SO$_2$Me |
| A1-97 | Cl | Me | pyrazol-1-yl | SO$_2$Me |
| A1-98 | Me | Me | 1,2,3-triazol-1-yl | SO$_2$Me |
| A1-99 | Cl | Me | 1,2,3-triazol-1-yl | SO$_2$Me |
| A1-100 | Me | Me | 4-methoxypyrazol-1-yl | SO$_2$Me |
| A1-101 | Et | Me | 4-methoxypyrazol-1-yl | SO$_2$Me |
| A1-102 | Cl | Me | 4-methoxypyrazol-1-yl | SO$_2$Me |
| A1-103 | c-Pr | Me | 4-methoxypyrazol-1-yl | SO$_2$Me |
| A1-104 | i-Pr | Cl | SMe | SO$_2$Me |
| A1-105 | Me | Cl | SMe | SO$_2$Me |
| A1-106 | NHAc | Cl | SMe | SO$_2$Me |

TABLE 2

Inventive compounds of the general formula (I) in which A is N

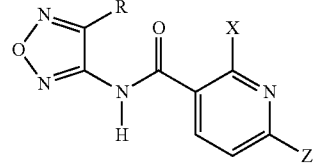

| Ex. No | R | X | Z |
|---|---|---|---|
| A2-1 | Me | Cl | CF$_3$ |
| A2-2 | Et | Cl | CF$_3$ |
| A2-3 | i-Pr | Cl | CF$_3$ |
| A2-4 | c-Pr | Cl | CF$_3$ |
| A2-5 | t-Bu | Cl | CF$_3$ |
| A2-6 | NH$_2$ | Cl | CF$_3$ |
| A2-7 | NHAc | Cl | CF$_3$ |
| A2-8 | 1,2,4-triazol-1-yl | Cl | CF$_3$ |
| A2-9 | Cl | Cl | CF$_3$ |
| A2-10 | Br | Cl | CF$_3$ |
| A2-11 | OMe | Cl | CF$_3$ |
| A2-12 | Me | Cl | Cl |
| A2-13 | Me | Me | CF$_3$ |
| A2-14 | Et | Me | CF$_3$ |
| A2-15 | c-Pr | Me | CF$_3$ |
| A2-16 | i-Pr | Me | CF$_3$ |
| A2-17 | Br | Me | CF$_3$ |
| A2-18 | OMe | Me | CF$_3$ |
| A2-19 | 1,2,4-triazol-1-yl | Me | CF$_3$ |
| A2-20 | OMe | Me | CF$_3$ |
| A2-21 | Me | Br | CF$_3$ |
| A2-22 | Me | CH$_2$OMe | CF$_3$ |
| A2-23 | Et | CH$_2$OMe | CF$_3$ |
| A2-24 | NHAc | CH$_2$OMe | CF$_3$ |
| A2-25 | 1,2,4-triazol-1-yl | CH$_2$OMe | CF$_3$ |
| A2-26 | NH$_2$ | CH$_2$OMe | CF$_3$ |
| A2-27 | Me | CH$_2$-1,2-thiazolidine-1,1-dioxid-1-yl | CF$_3$ |
| A2-28 | c-Pr | CH$_2$-1,2-thiazolidine-1,1-dioxid-1-yl | CF$_3$ |
| A2-29 | t-Bu | CH$_2$-1,2-thiazolidine-1,1-dioxid-1-yl | CF$_3$ |
| A2-30 | NHAc | CH$_2$-1,2-thiazolidine-1,1-dioxid-1-yl | CF$_3$ |
| A2-31 | NH$_2$ | CH$_2$-1,2-thiazolidine-1,1-dioxid-1-yl | CF$_3$ |
| A2-32 | Et | CH$_2$-1,2-thiazolidine-1,1-dioxid-1-yl | CF$_3$ |
| A2-33 | Me | CH$_2$-3-methylimidazolidin-2-on-1-yl | CF$_3$ |
| A2-34 | t-Bu | CH$_2$-3-methylimidazolidin-2-on-1-yl | CF$_3$ |
| A2-35 | Me | CH$_2$OCH$_2$CH$_2$OMe | CF$_3$ |
| A2-36 | t-Bu | CH$_2$OCH$_2$CH$_2$OMe | CF$_3$ |

The application rate of the herbicides of the general formula (I) (A) can vary within a wide range with the outdoor conditions, such as temperature, humidity and the type of herbicide used, for example between 0.001 g and 2000 g a.i./ha (ai/ha hereinafter means "active ingredient per hectare"=based on 100% active ingredient).

In the case of pre- and post-emergence applications at application rates of 0.01 g to 1000 g a.i./ha of the herbicides of the general formula (I) (A), a relatively broad spectrum of harmful plants, for example annual and perennial mono- or dicotyledonous weeds, and of unwanted crop plants is controlled. For the inventive combinations, the application rates are generally relatively low, for example in the range from 0.1 g to 800 g a.i./ha, preferably 1 g to 500 g a.i./ha, more preferably 10 g to 400 g a.i./ha.

The herbicides of the general formula (I) are suitable for control of harmful plants, for example, in plant crops, for example in economically important farm crops, e.g. monocotyledonous farm crops such as cereals (e.g. wheat, barley, rye, oats), rice, corn, millet/sorghum, or dicotyledonous farm crops such as sugar beet, oilseed rape, cotton, sunflower and legumes, for example of the genera *Glycine* (e.g. *Glycine max.* (soya) such as non-transgenic *Glycine max.* (e.g. conventional varieties such as STS varieties) or transgenic *Gly-*

*cine max.* (e.g. RR soya or LL soya) and crosses thereof), *Phaseolus, Pisum, Vicia* and *Arachis*, or vegetable crops from various botanic groups, such as potato, leek, cabbage, carrot, tomato, onion, and permanent crops and plantation crops such as pome fruit and stone fruit, berries, grapes, hevea, bananas, sugar cane, coffee, tea, citrus, nut plantations, lawns, palm crops and forestry crops. For the use of the inventive herbicide-safener combinations (A)+(B), these crops are likewise preferred, particular preference being given to use in cereals (e.g. wheat, barley, rye, oats), rice, corn, millet/sorghum, sugar beet, sugar cane, sunflower, oilseed rape and cotton. The herbicide-safener combinations (A)+(B) are also usable in tolerant and nontolerant mutant crops and tolerant and nontolerant transgenic crops, preferably of corn, rice, cereals, oilseed rape and soya, for example those which are resistant to imidazolinone herbicides, atrazine, glufosinate or glyphosate.

The compounds of the general formula (I) are known from EP0173657 and from EP 09012169.0, which has an earlier priority date but was yet to be published at the priority date of the present application, and can be obtained by the processes described therein.

The safeners present as component (B) are understood to mean compounds suitable for reducing phytotoxic effects of active ingredients in crop protection compositions, such as herbicides, on crop plants.

In the context of the present invention, the compounds of the general formula (I) are combined with the following safener compounds:

S1) Compounds from the group of heterocyclic carboxylic acid derivatives:

S1$^a$) Compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

S1$^b$) Derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

S1$^c$) Derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described, for example, in EP-A-268554;

S1$^d$) Compounds of the triazolecarboxylic acid type (S1$^d$), preferably compounds such as fenchlorazole (ethyl ester), i.e. ethyl 1-(2,4-dichlorophenyl)-5-trichloromethyl-1H-1,2,4-triazole-3-carboxylate (S1-7), and related compounds, as described in EP-A-174 562 and EP-A-346 620;

S1$^e$) Compounds of the 5-benzyl- or 5-phenyl-2-isoxazoline-3-carboxylic acid type or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in patent application WO-A-95/07897.

S2) Compounds from the group of the 8-quinolinyloxy derivatives (S2):

S2$^a$) Compounds of the 8-quinolinoxyacetic acid type (S2$^a$), preferably 1-methylhexyl(5-chloro-8-quinolinoxy)acetate ("cloquintocet-mexyl") (S2-1), 1,3-dimethylbut-1-yl(5-chloro-8-quinolinoxy)acetate (S2-2), 4-allyloxybutyl(5-chloro-8-quinolinoxy)acetate (S2-3), 1-allyloxyprop-2-yl (5-chloro-8-quinolinoxy)acetate (S2-4), ethyl(5-chloro-8-quinolinoxy)acetate (S2-5), methyl(5-chloro-8-quinolinoxy)acetate (S2-6), allyl(5-chloro-8-quinolinoxy) acetate (S2-7), 2-(2-propylideneiminoxy)-1-ethyl(5-chloro-8-quinolinoxy)acetate (S2-8), 2-oxoprop-1-yl(5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

S2$^b$) Compounds of the (5-chloro-8-quinolinoxy)malonic acid type (S2$^b$), preferably compounds such as diethyl(5-chloro-8-quinolinoxy)malonate, diallyl(5-chloro-8-quinolinoxy)malonate, methyl ethyl(5-chloro-8-quinolinoxy)malonate and related compounds, as described in EP-A-0 582 198.

S3) Active ingredients of the dichloroacetamide type (S3), which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N—[(allylaminocarbonyl)methyl] dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) (synonymously: "BAS145138" or "LAB145138") (RS)-1-dichloroacetyl-3,3,8a-trimethylperhydropyrrolo[1,2-a]pyrimidin-6-one from BASF (S3-9), "furilazole" or "MON 13900" ((RS)-3-dichloroacetyl-5-(2-furyl)-2,2-dimethyloxazolidine) (S3-10); and the (R) isomer thereof (S3-11).

S4) Compounds from the class of the acylsulfonamides (S4):

S4$^a$) N-Acylsulfonamides of the formula (S4$^a$) and salts thereof, as described in WO-A-97/45016,

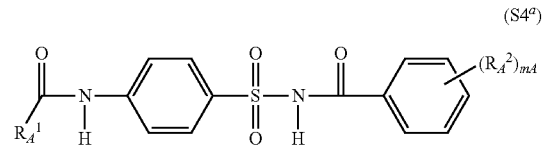

(S4$^a$)

in which $R_A^1$ is $(C_1-C_6)$-alkyl or $(C_3-C_6)$-cycloalkyl, where these radicals are substituted by $V_A$ substituents from the group of halogen, $(C_1-C_4)$-alkoxy, $(C_1-C_6)$-haloalkoxy and (C₁-C₄)-alkylthio and, in the cyclic radicals, also by (C₁-C₄)-alkyl and (C₁-C₄)-haloalkyl;

$R_A^2$ is halogen, (C₁-C₄)-alkyl, (C₁-C₄)-alkoxy, CF₃;

$m_A$ is 1 or 2;

$v_A$ is 0, 1, 2 or 3.

S4ᵇ) Compounds of the 4-(benzoylsulfamoyl)benzamide type of the formula (S4ᵇ) and salts thereof, as described in WO-A-99/16744,

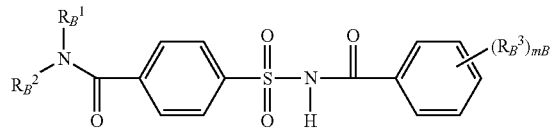
(S4ᵇ)

in which $R_B^1$, $R_B^2$ are each independently hydrogen, (C₁-C₆)-alkyl, (C₃-C₆)-cycloalkyl, (C₃-C₆)-alkenyl or (C₃-C₆)-alkynyl, $R_B^3$ is halogen, (C₁-C₄)-alkyl, (C₁-C₄)-haloalkyl or (C₁-C₄)-alkoxy and $m_B$ is 1 or 2, for example those in which $R_B^1$=cyclopropyl, $R_B^2$=hydrogen and ($R_B^3$)=2-OMe (S4-1, "cyprosulfamide"), $R_B^1$=cyclopropyl, $R_B^2$=hydrogen and ($R_B^3$)=5-C$_{1-2}$—OMe (S4-2), $R_B^1$=ethyl, $R_B^2$=hydrogen and ($R_B^3$)=2-OMe (S4-3), $R_B^1$=isopropyl, $R_B^2$=hydrogen and ($R_B^3$)=5-C$_{1-2}$—OMe (S4-4) and $R_B^1$=isopropyl, $R_B^2$=hydrogen and ($R_B^3$)=2-OMe (S4-5).

S4ᶜ) Compounds from the class of the benzoylsulfamoylphenylureas of the formula (S4ᶜ), as described in EP-A-365484,

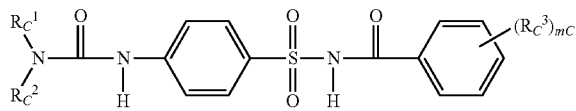
(S4ᶜ)

in which $R_C^1$, $R_C^2$ are each independently hydrogen, (C₁-C₈)-alkyl, (C₃-C₈)-cycloalkyl, (C₃-C₆)-alkenyl or (C₃-C₆)-alkynyl, $R_C^3$ is halogen, (C₁-C₄)-alkyl, (C₁-C₄)-alkoxy or CF₃;

$m_C$ is 1 or 2;

for example

1-[4-(N-2-methoxybenzoylsulfamoyl)phenyl]-3-methylurea (S4-6), 1-[4-(N-2-methoxybenzoylsulfamoyl) phenyl]-3,3-dimethylurea, 1-[4-(N-4,5-dimethylbenzoylsulfamoyl)phenyl]-3-methylurea.

S4ᵈ) Compounds of the N-phenylsulfonylterephthalamide type of the following formula (S4ᵈ) and salts thereof, which are known, for example, from CN 101838227,

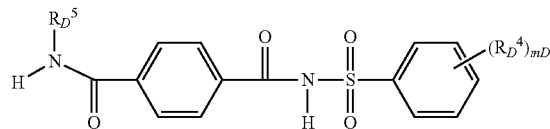
(S4ᵈ)

in which $R_D^4$ is halogen, (C₁-C₄)-alkyl, (C₁-C₄)-alkoxy or CF₃, $m_D$ is 1 or 2;

$R_D^5$ is hydrogen, (C₁-C₆)-alkyl, (C₃-C₆)-cycloalkyl, (C₂-C₆)-alkenyl, (C₂-C₆)-alkynyl or (C₅-C₆)-cycloalkenyl.

S5) Active ingredients from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of the diphenylmethoxyacetic acid derivatives (S7), for example methyl diphenylmethoxyacetate (CAS Reg. No. 41858-19-9) (S7-1), ethyl diphenylmethoxyacetate or diphenylmethoxyacetic acid, as described in WO-A-98/38856.

S8) Compounds of the formula (S8) as described in WO-A-98/27049

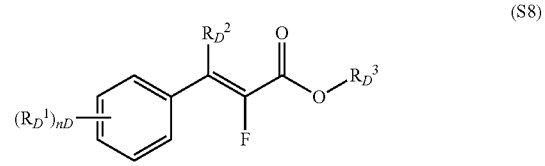
(S8)

in which $R_D^1$ is halogen, (C₁-C₄)-alkyl, (C₁-C₄)-haloalkyl, (C₁-C₄)-alkoxy, (C₁-C₄)-haloalkoxy, $R_D^2$ is hydrogen or (C₁-C₄)-alkyl, $R_D^3$ is hydrogen, (C₁-C₈)-alkyl, (C₂-C₄)-alkenyl, (C₂-C₄)-alkynyl or aryl, where each of the aforementioned carbon-containing radicals is unsubstituted or substituted by one or more, preferably up to three identical or different radicals from the group consisting of halogen and alkoxy; or salts thereof, $n_D$ is 0, 1 or 2.

S9) Active ingredients from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999/000020.

S10) Compounds of the formula (S10ᵃ) or (S10ᵇ) as described in WO-A-2007/023719 and WO-A-2007/023764,

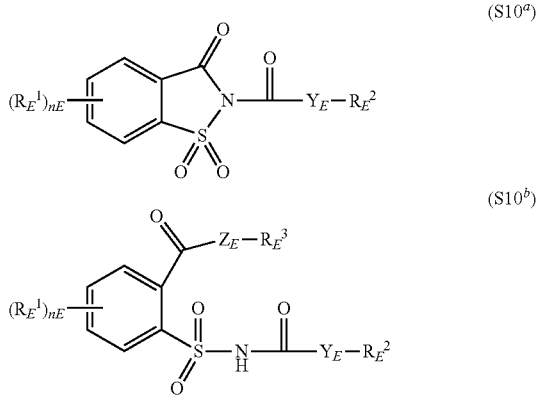

in which
$R_E^1$ is halogen, $(C_1-C_4)$-alkyl, methoxy, nitro, cyano, $CF_3$, $OCF_3$,
$Y_E$, $Z_E$ are each independently O or S,
$n_E$ is 0, 1, 2, 3 or 4,
$R_E^2$ is $(C_1-C_{16})$-alkyl, $(C_2-C_6)$-alkenyl, $(C_3-C_6)$-cycloalkyl, aryl, benzyl or halobenzyl,
$R_E^3$ is hydrogen or $(C_1-C_6)$-alkyl.

S11) Active ingredients of the oxyimino compound type (S11), which are known as seed-dressing compositions, for example "oxabetrinil" ((Z)-1,3-dioxolan-2-yl-methoxy-imino(phenyl)acetonitrile) (S11-1), which is known as a seed-dressing safener for millet/sorghum against metolachlor damage, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino (phenyl)acetonitrile) (S11-3), which is known as a seed-dressing safener for millet/sorghum against metolachlor damage.

S12) Active ingredients from the class of the isothiochromanones (S12), for example methyl[(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as a seed-dressing safener for corn against thiocarbamate herbicide damage,
"fenclorim" (4,6-dichloro-2-phenylpyrimidine) (S13-2), which is known as a safener for pretilachlor in sown rice,
"flurazole" (benzyl 2-chloro-4-trifluoromethyl-1,3-thiazole-5-carboxylate) (S13-3), which is known as a seed-dressing safener for millet/sorghum against alachlor and metolachlor damage,
"CL 304415" (CAS Reg. No.: 31541-57-8) (4-carboxy-3,4-dihydro-2H-1-benzopyran-4-acetic acid) (S13-4) from American Cyanamid, which is known as a safener for corn against imidazolinone damage,
"MG 191" (CAS Reg. No. 96420-72-3) (2-dichloromethyl-2-methyl-1,3-dioxolane) (S13-5) from Nitrokemia, which is known as a safener for corn,
"MG-838" (CAS Reg. No.: 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenyl phosphorothioate) (S13-8), "mephenate" (4-chlorophenyl methylcarbamate) (S13-9).

S14) Active ingredients which, in addition to herbicidal action against harmful plants, also have safener action on crop plants such as rice, for example "dimepiperate" or "MY-93" (S-1-methyl-1-phenylethylpiperidine-1-carbothioate), which is known as a safener for rice against damage by the herbicide molinate (S14-1),
"daimuron" or "SK 23" (1-(1-methyl-1-phenylethyl)-3-p-tolylurea), which is known as a safener for rice against damage by the herbicide imazosulfuron (S14-2),
"cumyluron"="JC-940" (3-(2-chlorophenylmethyl)-1-(1-methyl-1-phenylethyl)urea, see JP-A-60087254), which is known as a safener for rice against damage by some herbicides (S14-3),
"methoxyphenone" or "NK 049" (3,3'-dimethyl-4-methoxybenzophenone), which is known as a safener for rice against damage by some herbicides,
"CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof as described in WO-A-2008/131861 and WO-A-2008/131860

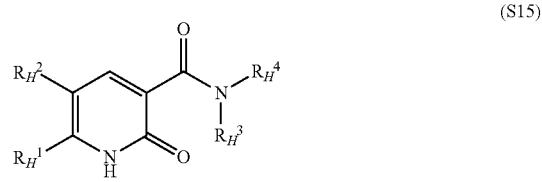

in which
$R_H^1$ is a $(C_1-C_6)$-haloalkyl radical,
$R_H^2$ is hydrogen or halogen,
$R_H^3$, $R_H^4$ are each independently hydrogen, $(C_1-C_{16})$-alkyl, $(C_2-C_{16})$-alkenyl or $(C_2-C_{16})$-alkynyl,
where each of the 3 latter radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted,
or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring,
where each of the 4 latter radicals is unsubstituted or substituted by one or more radicals from the group of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or
$R_H^3$ and $R_H^4$ together with the directly bonded nitrogen atom form a four- to eight-membered heterocyclic ring which, in addition to the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

The documents cited contain detailed information regarding preparation processes and starting materials, and name preferred compounds. These documents are explicitly incorporated by reference into this description.

Safeners of particular significance are S1-1, S1-7, S1-11, S2-1, S3-1, S3-2, S3-4, S3-7, S3-8, S3-10, S3-11, S4-1, S4-5, S4-6, S11-1, S11-2, S11-3, S13-1, S13-2, S13-3, S13-8, S14-1, S14-2 and S14-3.

Examples of preferred combinations of active herbicidal ingredients (A) and safeners (B) are given in the following overview:

(A1-1)+(S1-1); (A1-1)+(S1-7); (A1-1)+(S1-11); (A1-1)+(S2-1); (A1-1)+(S3-1); (A1-1)+(S3-2); (A1-1)+(S3-4); (A1-1)+(S3-7); (A1-1)+(S3-8); (A1-1)+(S3-10); (A1-1)+(S3-11); (A1-1)+(S4-1); (A1-1)+(S4-5); (A1-1)+(S4-6); (A1-1)+(S11-1); (A1-1)+(S11-2); (A1-1)+(S11-3); (A1-1)+(S13-1); (A1-1)+(S13-2); (A1-1)+(S13-3); (A1-1)+(S13-8); (A1-1)+(S14-1); (A1-1)+(S14-2); (A1-1)+(S14-3); (A1-2)+(S1-1); (A1-2)+(S1-7); (A1-2)+(S1-11); (A1-2)+(S2-1); (A1-2)+(S3-1); (A1-2)+(S3-2); (A1-2)+(S3-4); (A1-2)+(S3-7); (A1-2)+(S3-8); (A1-2)+(S3-10); (A1-2)+(S3-11); (A1-2)+(S4-1); (A1-2)+(S4-5); (A1-2)+(S4-6); (A1-2)+(S11-1); (A1-2)+(S11-2); (A1-2)+(S11-3); (A1-2)+(S13-1); (A1-2)+(S13-2); (A1-2)+(S13-3); (A1-2)+(S13-8); (A1-2)+(S14-1); (A1-2)+(S14-2); (A1-2)+(S14-3); (A1-3)+(S1-1); (A1-3)+(S1-7); (A1-3)+(S1-11); (A1-3)+(S2-1); (A1-3)+(S3-1); (A1-3)+(S3-2); (A1-3)+(S3-4); (A1-3)+(S3-7); (A1-3)+(S3-8); (A1-3)+(S3-10); (A1-3)+(S3-11); (A1-3)+(S4-1); (A1-3)+(S4-5); (A1-3)+(S4-6); (A1-3)+(S11-1); (A1-3)+(S11-2); (A1-3)+(S11-3); (A1-3)+(S13-1); (A1-3)+(S13-2); (A1-3)+(S13-3); (A1-3)+(S13-8); (A1-3)+(S14-1); (A1-3)+(S14-2); (A1-3)+(S14-3); (A1-4)+(S1-1); (A1-4)+(S1-7); (A1-4)+(S1-11); (A1-4)+(S2-1); (A1-4)+(S3-1); (A1-4)+(S3-2); (A1-4)+(S3-4); (A1-4)+(S3-7); (A1-4)+(S3-8); (A1-4)+(S3-10); (A1-4)+(S3-11); (A1-4)+(S4-1); (A1-4)+(S4-5); (A1-4)+(S4-6); (A1-4)+(S11-1); (A1-4)+(S11-2); (A1-4)+(S11-3); (A1-4)+(S13-1); (A1-4)+(S13-2); (A1-4)+(S13-3); (A1-4)+(S13-8); (A1-4)+(S14-1); (A1-4)+(S14-2); (A1-4)+(S14-3); (A1-5)+(S1-1); (A1-5)+(S1-7); (A1-5)+(S1-11); (A1-5)+(S2-1); (A1-5)+(S3-1); (A1-5)+(S3-2); (A1-5)+(S3-4); (A1-5)+(S3-7); (A1-5)+(S3-8); (A1-5)+(S3-10); (A1-5)+(S3-11); (A1-5)+(S4-1); (A1-5)+(S4-5); (A1-5)+(S4-6); (A1-5)+(S11-1); (A1-5)+(S11-2); (A1-5)+(S11-3); (A1-5)+(S13-1); (A1-5)+(S13-2); (A1-5)+(S13-3); (A1-5)+(S13-8); (A1-5)+(S14-1); (A1-5)+(S14-2); (A1-5)+(S14-3); (A1-6)+(S1-1); (A1-6)+(S1-7); (A1-6)+(S1-11); (A1-6)+(S2-1); (A1-6)+(S3-1); (A1-6)+(S3-2); (A1-6)+(S3-4); (A1-6)+(S3-7); (A1-6)+(S3-8); (A1-6)+(S3-10); (A1-6)+(S3-11); (A1-6)+(S4-1); (A1-6)+(S4-5); (A1-6)+(S4-6); (A1-6)+(S11-1); (A1-6)+(S11-2); (A1-6)+(S11-3); (A1-6)+(S13-1); (A1-6)+(S13-2); (A1-6)+(S13-3); (A1-6)+(S13-8); (A1-6)+(S14-1); (A1-6)+(S14-2); (A1-6)+(S14-3); (A1-7)+(S1-1); (A1-7)+(S1-7); (A1-7)+(S1-11); (A1-7)+(S2-1); (A1-7)+(S3-1); (A1-7)+(S3-2); (A1-7)+(S3-4); (A1-7)+(S3-7); (A1-7)+(S3-8); (A1-7)+(S3-10); (A1-7)+(S3-11); (A1-7)+(S4-1); (A1-7)+(S4-5); (A1-7)+(S4-6); (A1-7)+(S11-1); (A1-7)+(S11-2); (A1-7)+(S11-3); (A1-7)+(S13-1); (A1-7)+(S13-2); (A1-7)+(S13-3); (A1-7)+(S13-8); (A1-7)+(S14-1); (A1-7)+(S14-2); (A1-7)+(S14-3); (A1-8)+(S1-1); (A1-8)+(S1-7); (A1-8)+(S1-11); (A1-8)+(S2-1); (A1-8)+(S3-1); (A1-8)+(S3-2); (A1-8)+(S3-4); (A1-8)+(S3-7); (A1-8)+(S3-8); (A1-8)+(S3-10); (A1-8)+(S3-11); (A1-8)+(S4-1); (A1-8)+(S4-5); (A1-8)+(S4-6); (A1-8)+(S11-1); (A1-8)+(S11-2); (A1-8)+(S11-3); (A1-8)+(S13-1); (A1-8)+(S13-2); (A1-8)+(S13-3); (A1-8)+(S13-8); (A1-8)+(S14-1); (A1-8)+(S14-2); (A1-8)+(S14-3); (A1-9)+(S1-1); (A1-9)+(S1-7); (A1-9)+(S1-11); (A1-9)+(S2-1); (A1-9)+(S3-1); (A1-9)+(S3-2); (A1-9)+(S3-4); (A1-9)+(S3-7); (A1-9)+(S3-8); (A1-9)+(S3-10); (A1-9)+(S3-11); (A1-9)+(S4-1); (A1-9)+(S4-5); (A1-9)+(S4-6); (A1-9)+(S11-1); (A1-9)+(S11-2); (A1-9)+(S11-3); (A1-9)+(S13-1); (A1-9)+(S13-2); (A1-9)+(S13-3); (A1-9)+(S13-8); (A1-9)+(S14-1); (A1-9)+(S14-2); (A1-9)+(S14-3); (A1-10)+(S1-1); (A1-10)+(S1-7); (A1-10)+(S1-11); (A1-10)+(S2-1); (A1-10)+(S3-1); (A1-10)+(S3-2); (A1-10)+(S3-4); (A1-10)+(S3-7); (A1-10)+(S3-8); (A1-10)+(S3-10); (A1-10)+(S3-11); (A1-10)+(S4-1); (A1-10)+(S4-5); (A1-10)+(S4-6); (A1-10)+(S11-1); (A1-10)+(S11-2); (A1-10)+(S11-3); (A1-10)+(S13-1); (A1-10)+(S13-2); (A1-10)+(S13-3); (A1-10)+(S13-8); (A1-10)+(S14-1); (A1-10)+(S14-2); (A1-10)+(S14-3); (A1-11)+(S1-1); (A1-11)+(S1-7); (A1-11)+(S1-11); (A1-11)+(S2-1); (A1-11)+(S3-1); (A1-11)+(S3-2); (A1-11)+(S3-4); (A1-11)+(S3-7); (A1-11)+(S3-8); (A1-11)+(S3-10); (A1-11)+(S3-11); (A1-11)+(S4-1); (A1-11)+(S4-5); (A1-11)+(S4-6); (A1-11)+(S11-1); (A1-11)+(S11-2); (A1-11)+(S11-3); (A1-11)+(S13-1); (A1-11)+(S13-2); (A1-11)+(S13-3); (A1-11)+(S13-8); (A1-11)+(S14-1); (A1-11)+(S14-2); (A1-11)+(S14-3); (A1-12)+(S1-1); (A1-12)+(S1-7); (A1-12)+(S1-11); (A1-12)+(S2-1); (A1-12)+(S3-1); (A1-12)+(S3-2); (A1-12)+(S3-4); (A1-12)+(S3-7); (A1-12)+(S3-8); (A1-12)+(S3-10); (A1-12)+(S3-11); (A1-12)+(S4-1); (A1-12)+(S4-5); (A1-12)+(S4-6); (A1-12)+(S11-1); (A1-12)+(S11-2); (A1-12)+(S11-3); (A1-12)+(S13-1); (A1-12)+(S13-2); (A1-12)+(S13-3); (A1-12)+(S13-8); (A1-12)+(S14-1); (A1-12)+(S14-2); (A1-12)+(S14-3); (A1-13)+(S1-1); (A1-13)+(S1-7); (A1-13)+(S1-11); (A1-13)+(S2-1); (A1-13)+(S3-1); (A1-13)+(S3-2); (A1-13)+(S3-4); (A1-13)+(S3-7); (A1-13)+(S3-8); (A1-13)+(S3-10); (A1-13)+(S3-11); (A1-13)+(S4-1); (A1-13)+(S4-5); (A1-13)+(S4-6); (A1-13)+(S11-1); (A1-13)+(S11-2); (A1-13)+(S11-3); (A1-13)+(S13-1); (A1-13)+(S13-2); (A1-13)+(S13-3); (A1-13)+(S13-8); (A1-13)+(S14-1); (A1-13)+(S14-2); (A1-13)+(S14-3); (A1-14)+(S1-1); (A1-14)+(S1-7); (A1-14)+(S1-11); (A1-14)+(S2-1); (A1-14)+(S3-1); (A1-14)+(S3-2); (A1-14)+(S3-4); (A1-14)+(S3-7); (A1-14)+(S3-8); (A1-14)+(S3-10); (A1-14)+(S3-11); (A1-14)+(S4-1); (A1-14)+(S4-5); (A1-14)+(S4-6); (A1-14)+(S11-1); (A1-14)+(S11-2); (A1-14)+(S11-3); (A1-14)+(S13-1); (A1-14)+(S13-2); (A1-14)+(S13-3); (A1-14)+(S13-8); (A1-14)+(S14-1); (A1-14)+(S14-2); (A1-14)+(S14-3); (A1-15)+(S1-1); (A1-15)+(S1-7); (A1-15)+(S1-11); (A1-15)+(S2-1); (A1-15)+(S3-1); (A1-15)+(S3-2); (A1-15)+(S3-4); (A1-15)+(S3-7); (A1-15)+(S3-8); (A1-15)+(S3-10); (A1-15)+(S3-11); (A1-15)+(S4-1); (A1-15)+(S4-5); (A1-15)+(S4-6); (A1-15)+(S11-1); (A1-15)+(S11-2); (A1-15)+(S11-3); (A1-15)+(S13-1); (A1-15)+(S13-2); (A1-15)+(S13-3); (A1-15)+(S13-8); (A1-15)+(S14-1); (A1-15)+(S14-2); (A1-15)+(S14-3); (A1-16)+(S1-1); (A1-16)+(S1-7); (A1-16)+(S1-11); (A1-16)+(S2-1); (A1-16)+(S3-1); (A1-16)+(S3-2); (A1-16)+(S3-4); (A1-16)+(S3-7); (A1-16)+(S3-8); (A1-16)+(S3-10); (A1-16)+(S3-11); (A1-16)+(S4-1); (A1-16)+(S4-5); (A1-16)+(S4-6); (A1-16)+(S11-1); (A1-16)+(S11-2); (A1-16)+(S11-3); (A1-16)+(S13-1); (A1-16)+(S13-2); (A1-16)+(S13-3); (A1-16)+(S13-8); (A1-16)+(S14-1); (A1-16)+(S14-2); (A1-16)+(S14-3); (A1-17)+(S1-1); (A1-17)+(S1-7); (A1-17)+(S1-11); (A1-17)+(S2-1); (A1-17)+(S3-1); (A1-17)+(S3-2); (A1-17)+(S3-4); (A1-17)+(S3-7); (A1-17)+(S3-8); (A1-17)+(S3-10); (A1-17)+(S3-11); (A1-17)+(S4-1); (A1-17)+(S4-5); (A1-17)+(S4-6); (A1-17)+(S11-1); (A1-17)+(S11-2); (A1-17)+(S11-3); (A1-17)+(S13-1); (A1-17)+(S13-2); (A1-17)+(S13-3); (A1-17)+(S13-8); (A1-17)+(S14-1); (A1-17)+(S14-2); (A1-17)+(S14-3); (A1-18)+(S1-1); (A1-18)+(S1-7); (A1-18)+(S1-11); (A1-18)+(S2-1); (A1-18)+(S3-1);

(A1-18)+(S3-2); (A1-18)+(S3-4); (A1-18)+(S3-7); (A1-18)+(S3-8); (A1-18)+(S3-10); (A1-18)+(S3-11); (A1-18)+(S4-1); (A1-18)+(S4-5); (A1-18)+(S4-6); (A1-18)+(S11-1); (A1-18)+(S11-2); (A1-18)+(S11-3); (A1-18)+(S13-1); (A1-18)+(S13-2); (A1-18)+(S13-3); (A1-18)+(S13-8); (A1-18)+(S14-1); (A1-18)+(S14-2); (A1-18)+(S14-3); (A1-19)+(S1-1); (A1-19)+(S1-7); (A1-19)+(S1-11); (A1-19)+(S2-1); (A1-19)+(S3-1); (A1-19)+(S3-2); (A1-19)+(S3-4); (A1-19)+(S3-7); (A1-19)+(S3-8); (A1-19)+(S3-10); (A1-19)+(S3-11); (A1-19)+(S4-1); (A1-19)+(S4-5); (A1-19)+(S4-6); (A1-19)+(S11-1); (A1-19)+(S11-2); (A1-19)+(S11-3); (A1-19)+(S13-1); (A1-19)+(S13-2); (A1-19)+(S13-3); (A1-19)+(S13-8); (A1-19)+(S14-1); (A1-19)+(S14-2); (A1-19)+(S14-3); (A1-20)+(S1-1); (A1-20)+(S1-7); (A1-20)+(S1-11); (A1-20)+(S2-1); (A1-20)+(S3-1); (A1-20)+(S3-2); (A1-20)+(S3-4); (A1-20)+(S3-7); (A1-20)+(S3-8); (A1-20)+(S3-10); (A1-20)+(S3-11); (A1-20)+(S4-1); (A1-20)+(S4-5); (A1-20)+(S4-6); (A1-20)+(S11-1); (A1-20)+(S11-2); (A1-20)+(S11-3); (A1-20)+(S13-1); (A1-20)+(S13-2); (A1-20)+(S13-3); (A1-20)+(S13-8); (A1-20)+(S14-1); (A1-20)+(S14-2); (A1-20)+(S14-3); (A1-21)+(S1-1); (A1-21)+(S1-7); (A1-21)+(S1-11); (A1-21)+(S2-1); (A1-21)+(S3-1); (A1-21)+(S3-2); (A1-21)+(S3-4); (A1-21)+(S3-7); (A1-21)+(S3-8); (A1-21)+(S3-10); (A1-21)+(S3-11); (A1-21)+(S4-1); (A1-21)+(S4-5); (A1-21)+(S4-6); (A1-21)+(S11-1); (A1-21)+(S11-2); (A1-21)+(S11-3); (A1-21)+(S13-1); (A1-21)+(S13-2); (A1-21)+(S13-3); (A1-21)+(S13-8); (A1-21)+(S14-1); (A1-21)+(S14-2); (A1-21)+(S14-3); (A1-22)+(S1-1); (A1-22)+(S1-7); (A1-22)+(S1-11); (A1-22)+(S2-1); (A1-22)+(S3-1); (A1-22)+(S3-2); (A1-22)+(S3-4); (A1-22)+(S3-7); (A1-22)+(S3-8); (A1-22)+(S3-10); (A1-22)+(S3-11); (A1-22)+(S4-1); (A1-22)+(S4-5); (A1-22)+(S4-6); (A1-22)+(S11-1); (A1-22)+(S11-2); (A1-22)+(S11-3); (A1-22)+(S13-1); (A1-22)+(S13-2); (A1-22)+(S13-3); (A1-22)+(S13-8); (A1-22)+(S14-1); (A1-22)+(S14-2); (A1-22)+(S14-3); (A1-23)+(S1-1); (A1-23)+(S1-7); (A1-23)+(S1-11); (A1-23)+(S2-1); (A1-23)+(S3-1); (A1-23)+(S3-2); (A1-23)+(S3-4); (A1-23)+(S3-7); (A1-23)+(S3-8); (A1-23)+(S3-10); (A1-23)+(S3-11); (A1-23)+(S4-1); (A1-23)+(S4-5); (A1-23)+(S4-6); (A1-23)+(S11-1); (A1-23)+(S11-2); (A1-23)+(S11-3); (A1-23)+(S13-1); (A1-23)+(S13-2); (A1-23)+(S13-3); (A1-23)+(S13-8); (A1-23)+(S14-1); (A1-23)+(S14-2); (A1-23)+(S14-3); (A1-24)+(S1-1); (A1-24)+(S1-7); (A1-24)+(S1-11); (A1-24)+(S2-1); (A1-24)+(S3-1); (A1-24)+(S3-2); (A1-24)+(S3-4); (A1-24)+(S3-7); (A1-24)+(S3-8); (A1-24)+(S3-10); (A1-24)+(S3-11); (A1-24)+(S4-1); (A1-24)+(S4-5); (A1-24)+(S4-6); (A1-24)+(S11-1); (A1-24)+(S11-2); (A1-24)+(S11-3); (A1-24)+(S13-1); (A1-24)+(S13-2); (A1-24)+(S13-3); (A1-24)+(S13-8); (A1-24)+(S14-1); (A1-24)+(S14-2); (A1-24)+(S14-3); (A1-25)+(S1-1); (A1-25)+(S1-7); (A1-25)+(S1-11); (A1-25)+(S2-1); (A1-25)+(S3-1); (A1-25)+(S3-2); (A1-25)+(S3-4); (A1-25)+(S3-7); (A1-25)+(S3-8); (A1-25)+(S3-10); (A1-25)+(S3-11); (A1-25)+(S4-1); (A1-25)+(S4-5); (A1-25)+(S4-6); (A1-25)+(S11-1); (A1-25)+(S11-2); (A1-25)+(S11-3); (A1-25)+(S13-1); (A1-25)+(S13-2); (A1-25)+(S13-3); (A1-25)+(S13-8); (A1-25)+(S14-1); (A1-25)+(S14-2); (A1-25)+(S14-3); (A1-26)+(S1-1); (A1-26)+(S1-7); (A1-26)+(S1-11); (A1-26)+(S2-1); (A1-26)+(S3-1); (A1-26)+(S3-2); (A1-26)+(S3-4); (A1-26)+(S3-7); (A1-26)+(S3-8); (A1-26)+(S3-10); (A1-26)+(S3-11); (A1-26)+(S4-1); (A1-26)+(S4-5); (A1-26)+(S4-6); (A1-26)+(S11-1); (A1-26)+(S11-2); (A1-26)+(S11-3); (A1-26)+(S13-1); (A1-26)+(S13-2); (A1-26)+(S13-3); (A1-26)+(S13-8); (A1-26)+(S14-1); (A1-26)+(S14-2); (A1-26)+(S14-3); (A1-27)+(S1-1); (A1-27)+(S1-7); (A1-27)+(S1-11); (A1-27)+(S2-1); (A1-27)+(S3-1); (A1-27)+(S3-2); (A1-27)+(S3-4); (A1-27)+(S3-7); (A1-27)+(S3-8); (A1-27)+(S3-10); (A1-27)+(S3-11); (A1-27)+(S4-1); (A1-27)+(S4-5); (A1-27)+(S4-6); (A1-27)+(S11-1); (A1-27)+(S11-2); (A1-27)+(S11-3); (A1-27)+(S13-1); (A1-27)+(S13-2); (A1-27)+(S13-3); (A1-27)+(S13-8); (A1-27)+(S14-1); (A1-27)+(S14-2); (A1-27)+(S14-3); (A1-28)+(S1-1); (A1-28)+(S1-7); (A1-28)+(S1-11); (A1-28)+(S2-1); (A1-28)+(S3-1); (A1-28)+(S3-2); (A1-28)+(S3-4); (A1-28)+(S3-7); (A1-28)+(S3-8); (A1-28)+(S3-10); (A1-28)+(S3-11); (A1-28)+(S4-1); (A1-28)+(S4-5); (A1-28)+(S4-6); (A1-28)+(S11-1); (A1-28)+(S11-2); (A1-28)+(S11-3); (A1-28)+(S13-1); (A1-28)+(S13-2); (A1-28)+(S13-3); (A1-28)+(S13-8); (A1-28)+(S14-1); (A1-28)+(S14-2); (A1-28)+(S14-3); (A1-29)+(S1-1); (A1-29)+(S1-7); (A1-29)+(S1-11); (A1-29)+(S2-1); (A1-29)+(S3-1); (A1-29)+(S3-2); (A1-29)+(S3-4); (A1-29)+(S3-7); (A1-29)+(S3-8); (A1-29)+(S3-10); (A1-29)+(S3-11); (A1-29)+(S4-1); (A1-29)+(S4-5); (A1-29)+(S4-6); (A1-29)+(S11-1); (A1-29)+(S11-2); (A1-29)+(S11-3); (A1-29)+(S13-1); (A1-29)+(S13-2); (A1-29)+(S13-3); (A1-29)+(S13-8); (A1-29)+(S14-1); (A1-29)+(S14-2); (A1-29)+(S14-3); (A1-30)+(S1-1); (A1-30)+(S1-7); (A1-30)+(S1-11); (A1-30)+(S2-1); (A1-30)+(S3-1); (A1-30)+(S3-2); (A1-30)+(S3-4); (A1-30)+(S3-7); (A1-30)+(S3-8); (A1-30)+(S3-10); (A1-30)+(S3-11); (A1-30)+(S4-1); (A1-30)+(S4-5); (A1-30)+(S4-6); (A1-30)+(S11-1); (A1-30)+(S11-2); (A1-30)+(S11-3); (A1-30)+(S13-1); (A1-30)+(S13-2); (A1-30)+(S13-3); (A1-30)+(S13-8); (A1-30)+(S14-1); (A1-30)+(S14-2); (A1-30)+(S14-3); (A1-31)+(S1-1); (A1-31)+(S1-7); (A1-31)+(S1-11); (A1-31)+(S2-1); (A1-31)+(S3-1); (A1-31)+(S3-2); (A1-31)+(S3-4); (A1-31)+(S3-7); (A1-31)+(S3-8); (A1-31)+(S3-10); (A1-31)+(S3-11); (A1-31)+(S4-1); (A1-31)+(S4-5); (A1-31)+(S4-6); (A1-31)+(S11-1); (A1-31)+(S11-2); (A1-31)+(S11-3); (A1-31)+(S13-1); (A1-31)+(S13-2); (A1-31)+(S13-3); (A1-31)+(S13-8); (A1-31)+(S14-1); (A1-31)+(S14-2); (A1-31)+(S14-3); (A1-32)+(S1-1); (A1-32)+(S1-7); (A1-32)+(S1-11); (A1-32)+(S2-1); (A1-32)+(S3-1); (A1-32)+(S3-2); (A1-32)+(S3-4); (A1-32)+(S3-7); (A1-32)+(S3-8); (A1-32)+(S3-10); (A1-32)+(S3-11); (A1-32)+(S4-1); (A1-32)+(S4-5); (A1-32)+(S4-6); (A1-32)+(S11-1); (A1-32)+(S11-2); (A1-32)+(S11-3); (A1-32)+(S13-1); (A1-32)+(S13-2); (A1-32)+(S13-3); (A1-32)+(S13-8); (A1-32)+(S14-1); (A1-32)+(S14-2); (A1-32)+(S14-3); (A1-33)+(S1-1); (A1-33)+(S1-7); (A1-33)+(S1-11); (A1-33)+(S2-1); (A1-33)+(S3-1); (A1-33)+(S3-2); (A1-33)+(S3-4); (A1-33)+(S3-7); (A1-33)+(S3-8); (A1-33)+(S3-10); (A1-33)+(S3-11); (A1-33)+(S4-1); (A1-33)+(S4-5); (A1-33)+(S4-6); (A1-33)+(S11-1); (A1-33)+(S11-2); (A1-33)+(S11-3); (A1-33)+(S13-1); (A1-33)+(S13-2); (A1-33)+(S13-3); (A1-33)+(S13-8); (A1-33)+(S14-1); (A1-33)+(S14-2); (A1-33)+(S14-3); (A1-34)+(S1-1); (A1-34)+(S1-7); (A1-34)+(S1-11); (A1-34)+(S2-1); (A1-34)+(S3-1); (A1-34)+(S3-2); (A1-34)+(S3-4); (A1-34)+(S3-7); (A1-34)+(S3-8); (A1-34)+(S3-10); (A1-34)+(S3-11); (A1-34)+(S4-1); (A1-34)+(S4-5); (A1-34)+(S4-6); (A1-34)+(S11-1); (A1-34)+(S11-2); (A1-34)+(S11-3); (A1-34)+(S13-1); (A1-34)+(S13-2); (A1-34)+(S13-3); (A1-34)+(S13-8); (A1-34)+(S14-1); (A1-34)+(S14-2); (A1-34)+(S14-3); (A1-35)+(S1-1); (A1-35)+(S1-7); (A1-35)+(S1-11); (A1-35)+(S2-1); (A1-35)+(S3-1); (A1-35)+(S3-2); (A1-35)+(S3-4); (A1-35)+(S3-7); (A1-35)+(S3-8); (A1-35)+(S3-10); (A1-35)+(S3-11); (A1-35)+(S4-1); (A1-35)+(S4-5); (A1-35)+(S4-6); (A1-35)+(S11-1); (A1-35)+(S11-2); (A1-35)+(S11-3); (A1-35)+(S13-1); (A1-35)+(S13-2); (A1-35)+(S13-3); (A1-35)+(S13-8); (A1-35)+(S14-1); (A1-35)+(S14-2); (A1-35)+(S14-3); (A1-36)+(S1-1); (A1-36)+(S1-7); (A1-36)+(S1-11); (A1-36)+(S2-1); (A1-36)+(S3-1); (A1-36)+(S3-2); (A1-36)+(S3-4); (A1-36)+(S3-7); (A1-36)+(S3-8); (A1-36)+(S3-10); (A1-36)+(S3-11); (A1-36)+(S4-1); (A1-36)+(S4-5); (A1-36)+(S4-6); (A1-36)+(S11-1); (A1-36)+(S11-2); (A1-36)+(S11-

3); (A1-36)+(S13-1); (A1-36)+(S13-2); (A1-36)+(S13-3); (A1-36)+(S13-8); (A1-36)+(S14-1); (A1-36)+(S14-2); (A1-36)+(S14-3); (A1-37)+(S1-1); (A1-37)+(S1-7); (A1-37)+(S1-11); (A1-37)+(S2-1); (A1-37)+(S3-1); (A1-37)+(S3-2); (A1-37)+(S3-4); (A1-37)+(S3-7); (A1-37)+(S3-8); (A1-37)+(S3-10); (A1-37)+(S3-11); (A1-37)+(S4-1); (A1-37)+(S4-5); (A1-37)+(S4-6); (A1-37)+(S11-1); (A1-37)+(S11-2); (A1-37)+(S11-3); (A1-37)+(S13-1); (A1-37)+(S13-2); (A1-37)+(S13-3); (A1-37)+(S13-8); (A1-37)+(S14-1); (A1-37)+(S14-2); (A1-37)+(S14-3); (A1-38)+(S1-1); (A1-38)+(S1-7); (A1-38)+(S1-11); (A1-38)+(S2-1); (A1-38)+(S3-1); (A1-38)+(S3-2); (A1-38)+(S3-4); (A1-38)+(S3-7); (A1-38)+(S3-8); (A1-38)+(S3-10); (A1-38)+(S3-11); (A1-38)+(S4-1); (A1-38)+(S4-5); (A1-38)+(S4-6); (A1-38)+(S11-1); (A1-38)+(S11-2); (A1-38)+(S11-3); (A1-38)+(S13-1); (A1-38)+(S13-2); (A1-38)+(S13-3); (A1-38)+(S13-8); (A1-38)+(S14-1); (A1-38)+(S14-2); (A1-38)+(S14-3); (A1-39)+(S1-1); (A1-39)+(S1-7); (A1-39)+(S1-11); (A1-39)+(S2-1); (A1-39)+(S3-1); (A1-39)+(S3-2); (A1-39)+(S3-4); (A1-39)+(S3-7); (A1-39)+(S3-8); (A1-39)+(S3-10); (A1-39)+(S3-11); (A1-39)+(S4-1); (A1-39)+(S4-5); (A1-39)+(S4-6); (A1-39)+(S11-1); (A1-39)+(S11-2); (A1-39)+(S11-3); (A1-39)+(S13-1); (A1-39)+(S13-2); (A1-39)+(S13-3); (A1-39)+(S13-8); (A1-39)+(S14-1); (A1-39)+(S14-2); (A1-39)+(S14-3); (A1-40)+(S1-1); (A1-40)+(S1-7); (A1-40)+(S1-11); (A1-40)+(S2-1); (A1-40)+(S3-1); (A1-40)+(S3-2); (A1-40)+(S3-4); (A1-40)+(S3-7); (A1-40)+(S3-8); (A1-40)+(S3-10); (A1-40)+(S3-11); (A1-40)+(S4-1); (A1-40)+(S4-5); (A1-40)+(S4-6); (A1-40)+(S11-1); (A1-40)+(S11-2); (A1-40)+(S11-3); (A1-40)+(S13-1); (A1-40)+(S13-2); (A1-40)+(S13-3); (A1-40)+(S13-8); (A1-40)+(S14-1); (A1-40)+(S14-2); (A1-40)+(S14-3); (A1-41)+(S1-1); (A1-41)+(S1-7); (A1-41)+(S1-11); (A1-41)+(S2-1); (A1-41)+(S3-1); (A1-41)+(S3-2); (A1-41)+(S3-4); (A1-41)+(S3-7); (A1-41)+(S3-8); (A1-41)+(S3-10); (A1-41)+(S3-11); (A1-41)+(S4-1); (A1-41)+(S4-5); (A1-41)+(S4-6); (A1-41)+(S11-1); (A1-41)+(S11-2); (A1-41)+(S11-3); (A1-41)+(S13-1); (A1-41)+(S13-2); (A1-41)+(S13-3); (A1-41)+(S13-8); (A1-41)+(S14-1); (A1-41)+(S14-2); (A1-41)+(S14-3); (A1-42)+(S1-1); (A1-42)+(S1-7); (A1-42)+(S1-11); (A1-42)+(S2-1); (A1-42)+(S3-1); (A1-42)+(S3-2); (A1-42)+(S3-4); (A1-42)+(S3-7); (A1-42)+(S3-8); (A1-42)+(S3-10); (A1-42)+(S3-11); (A1-42)+(S4-1); (A1-42)+(S4-5); (A1-42)+(S4-6); (A1-42)+(S11-1); (A1-42)+(S11-2); (A1-42)+(S11-3); (A1-42)+(S13-1); (A1-42)+(S13-2); (A1-42)+(S13-3); (A1-42)+(S13-8); (A1-42)+(S14-1); (A1-42)+(S14-2); (A1-42)+(S14-3); (A1-43)+(S1-1); (A1-43)+(S1-7); (A1-43)+(S1-11); (A1-43)+(S2-1); (A1-43)+(S3-1); (A1-43)+(S3-2); (A1-43)+(S3-4); (A1-43)+(S3-7); (A1-43)+(S3-8); (A1-43)+(S3-10); (A1-43)+(S3-11); (A1-43)+(S4-1); (A1-43)+(S4-5); (A1-43)+(S4-6); (A1-43)+(S11-1); (A1-43)+(S11-2); (A1-43)+(S11-3); (A1-43)+(S13-1); (A1-43)+(S13-2); (A1-43)+(S13-3); (A1-43)+(S13-8); (A1-43)+(S14-1); (A1-43)+(S14-2); (A1-43)+(S14-3); (A1-44)+(S1-1); (A1-44)+(S1-7); (A1-44)+(S1-11); (A1-44)+(S2-1); (A1-44)+(S3-1); (A1-44)+(S3-2); (A1-44)+(S3-4); (A1-44)+(S3-7); (A1-44)+(S3-8); (A1-44)+(S3-10); (A1-44)+(S3-11); (A1-44)+(S4-1); (A1-44)+(S4-5); (A1-44)+(S4-6); (A1-44)+(S11-1); (A1-44)+(S11-2); (A1-44)+(S11-3); (A1-44)+(S13-1); (A1-44)+(S13-2); (A1-44)+(S13-3); (A1-44)+(S13-8); (A1-44)+(S14-1); (A1-44)+(S14-2); (A1-44)+(S14-3); (A1-45)+(S1-1); (A1-45)+(S1-7); (A1-45)+(S1-11); (A1-45)+(S2-1); (A1-45)+(S3-1); (A1-45)+(S3-2); (A1-45)+(S3-4); (A1-45)+(S3-7); (A1-45)+(S3-8); (A1-45)+(S3-10); (A1-45)+(S3-11); (A1-45)+(S4-1); (A1-45)+(S4-5); (A1-45)+(S4-6); (A1-45)+(S11-1); (A1-45)+(S11-2); (A1-45)+(S11-3); (A1-45)+(S13-1); (A1-45)+(S13-2); (A1-45)+(S13-3); (A1-45)+(S13-8); (A1-45)+(S14-1); (A1-45)+(S14-2); (A1-45)+(S14-3); (A1-46)+(S1-1); (A1-46)+(S1-7); (A1-46)+(S1-11); (A1-46)+(S2-1); (A1-46)+(S3-1); (A1-46)+(S3-2); (A1-46)+(S3-4); (A1-46)+(S3-7); (A1-46)+(S3-8); (A1-46)+(S3-10); (A1-46)+(S3-11); (A1-46)+(S4-1); (A1-46)+(S4-5); (A1-46)+(S4-6); (A1-46)+(S11-1); (A1-46)+(S11-2); (A1-46)+(S11-3); (A1-46)+(S13-1); (A1-46)+(S13-2); (A1-46)+(S13-3); (A1-46)+(S13-8); (A1-46)+(S14-1); (A1-46)+(S14-2); (A1-46)+(S14-3); (A1-47)+(S1-1); (A1-47)+(S1-7); (A1-47)+(S1-11); (A1-47)+(S2-1); (A1-47)+(S3-1); (A1-47)+(S3-2); (A1-47)+(S3-4); (A1-47)+(S3-7); (A1-47)+(S3-8); (A1-47)+(S3-10); (A1-47)+(S3-11); (A1-47)+(S4-1); (A1-47)+(S4-5); (A1-47)+(S4-6); (A1-47)+(S11-1); (A1-47)+(S11-2); (A1-47)+(S11-3); (A1-47)+(S13-1); (A1-47)+(S13-2); (A1-47)+(S13-3); (A1-47)+(S13-8); (A1-47)+(S14-1); (A1-47)+(S14-2); (A1-47)+(S14-3); (A1-48)+(S1-1); (A1-48)+(S1-7); (A1-48)+(S1-11); (A1-48)+(S2-1); (A1-48)+(S3-1); (A1-48)+(S3-2); (A1-48)+(S3-4); (A1-48)+(S3-7); (A1-48)+(S3-8); (A1-48)+(S3-10); (A1-48)+(S3-11); (A1-48)+(S4-1); (A1-48)+(S4-5); (A1-48)+(S4-6); (A1-48)+(S11-1); (A1-48)+(S11-2); (A1-48)+(S11-3); (A1-48)+(S13-1); (A1-48)+(S13-2); (A1-48)+(S13-3); (A1-48)+(S13-8); (A1-48)+(S14-1); (A1-48)+(S14-2); (A1-48)+(S14-3); (A1-49)+(S1-1); (A1-49)+(S1-7); (A1-49)+(S1-11); (A1-49)+(S2-1); (A1-49)+(S3-1); (A1-49)+(S3-2); (A1-49)+(S3-4); (A1-49)+(S3-7); (A1-49)+(S3-8); (A1-49)+(S3-10); (A1-49)+(S3-11); (A1-49)+(S4-1); (A1-49)+(S4-5); (A1-49)+(S4-6); (A1-49)+(S11-1); (A1-49)+(S11-2); (A1-49)+(S11-3); (A1-49)+(S13-1); (A1-49)+(S13-2); (A1-49)+(S13-3); (A1-49)+(S13-8); (A1-49)+(S14-1); (A1-49)+(S14-2); (A1-49)+(S14-3); (A1-50)+(S1-1); (A1-50)+(S1-7); (A1-50)+(S1-11); (A1-50)+(S2-1); (A1-50)+(S3-1); (A1-50)+(S3-2); (A1-50)+(S3-4); (A1-50)+(S3-7); (A1-50)+(S3-8); (A1-50)+(S3-10); (A1-50)+(S3-11); (A1-50)+(S4-1); (A1-50)+(S4-5); (A1-50)+(S4-6); (A1-50)+(S11-1); (A1-50)+(S11-2); (A1-50)+(S11-3); (A1-50)+(S13-1); (A1-50)+(S13-2); (A1-50)+(S13-3); (A1-50)+(S13-8); (A1-50)+(S14-1); (A1-50)+(S14-2); (A1-50)+(S14-3); (A1-51)+(S1-1); (A1-51)+(S1-7); (A1-51)+(S1-11); (A1-51)+(S2-1); (A1-51)+(S3-1); (A1-51)+(S3-2); (A1-51)+(S3-4); (A1-51)+(S3-7); (A1-51)+(S3-8); (A1-51)+(S3-10); (A1-51)+(S3-11); (A1-51)+(S4-1); (A1-51)+(S4-5); (A1-51)+(S4-6); (A1-51)+(S11-1); (A1-51)+(S11-2); (A1-51)+(S11-3); (A1-51)+(S13-1); (A1-51)+(S13-2); (A1-51)+(S13-3); (A1-51)+(S13-8); (A1-51)+(S14-1); (A1-51)+(S14-2); (A1-51)+(S14-3); (A1-52)+(S1-1); (A1-52)+(S1-7); (A1-52)+(S1-11); (A1-52)+(S2-1); (A1-52)+(S3-1); (A1-52)+(S3-2); (A1-52)+(S3-4); (A1-52)+(S3-7); (A1-52)+(S3-8); (A1-52)+(S3-10); (A1-52)+(S3-11); (A1-52)+(S4-1); (A1-52)+(S4-5); (A1-52)+(S4-6); (A1-52)+(S11-1); (A1-52)+(S11-2); (A1-52)+(S11-3); (A1-52)+(S13-1); (A1-52)+(S13-2); (A1-52)+(S13-3); (A1-52)+(S13-8); (A1-52)+(S14-1); (A1-52)+(S14-2); (A1-52)+(S14-3); (A1-53)+(S1-1); (A1-53)+(S1-7); (A1-53)+(S1-11); (A1-53)+(S2-1); (A1-53)+(S3-1); (A1-53)+(S3-2); (A1-53)+(S3-4); (A1-53)+(S3-7); (A1-53)+(S3-8); (A1-53)+(S3-10); (A1-53)+(S3-11); (A1-53)+(S4-1); (A1-53)+(S4-5); (A1-53)+(S4-6); (A1-53)+(S11-1); (A1-53)+(S11-2); (A1-53)+(S11-3); (A1-53)+(S13-1); (A1-53)+(S13-2); (A1-53)+(S13-3); (A1-53)+(S13-8); (A1-53)+(S14-1); (A1-53)+(S14-2); (A1-53)+(S14-3); (A1-54)+(S1-1); (A1-54)+(S1-7); (A1-54)+(S1-11); (A1-54)+(S2-1); (A1-54)+(S3-1); (A1-54)+(S3-2); (A1-54)+(S3-4); (A1-54)+(S3-7); (A1-54)+(S3-8); (A1-54)+(S3-10); (A1-54)+(S3-11); (A1-54)+(S4-1); (A1-54)+(S4-5); (A1-54)+(S4-6); (A1-54)+(S11-1); (A1-54)+(S11-2); (A1-54)+(S11-3); (A1-54)+(S13-1); (A1-54)+(S13-2); (A1-54)+(S13-3); (A1-54)+(S13-8); (A1-54)+(S14-1); (A1-54)+(S14-2); (A1-54)+(S14-3); (A1-55)+(S1-1); (A1-55)+(S1-7); (A1-55)+(S1-11); (A1-55)+(S2-1); (A1-

55)+(S3-1); (A1-55)+(S3-2); (A1-55)+(S3-7); (A1-55)+(S3-8); (A1-55)+(S3-10); (A1-55)+(S3-11); (A1-55)+(S4-1); (A1-55)+(S4-5); (A1-55)+(S4-6); (A1-55)+(S11-1); (A1-55)+(S11-2); (A1-55)+(S11-3); (A1-55)+(S13-1); (A1-55)+(S13-2); (A1-55)+(S13-3); (A1-55)+(S13-8); (A1-55)+(S14-1); (A1-55)+(S14-2); (A1-55)+(S14-3); (A1-56)+(S1-1); (A1-56)+(S1-7); (A1-56)+(S1-11); (A1-56)+(S2-1); (A1-56)+(S3-1); (A1-56)+(S3-2); (A1-56)+(S3-4); (A1-56)+(S3-7); (A1-56)+(S3-8); (A1-56)+(S3-10); (A1-56)+(S3-11); (A1-56)+(S4-1); (A1-56)+(S4-5); (A1-56)+(S4-6); (A1-56)+(S11-1); (A1-56)+(S11-2); (A1-56)+(S11-3); (A1-56)+(S13-1); (A1-56)+(S13-2); (A1-56)+(S13-3); (A1-56)+(S13-8); (A1-56)+(S14-1); (A1-56)+(S14-2); (A1-56)+(S14-3); (A1-57)+(S1-1); (A1-57)+(S1-7); (A1-57)+(S1-11); (A1-57)+(S2-1); (A1-57)+(S3-1); (A1-57)+(S3-2); (A1-57)+(S3-4); (A1-57)+(S3-7); (A1-57)+(S3-8); (A1-57)+(S3-10); (A1-57)+(S3-11); (A1-57)+(S4-1); (A1-57)+(S4-5); (A1-57)+(S4-6); (A1-57)+(S11-1); (A1-57)+(S11-2); (A1-57)+(S11-3); (A1-57)+(S13-1); (A1-57)+(S13-2); (A1-57)+(S13-3); (A1-57)+(S13-8); (A1-57)+(S14-1); (A1-57)+(S14-2); (A1-57)+(S14-3); (A1-58)+(S1-1); (A1-58)+(S1-7); (A1-58)+(S1-11); (A1-58)+(S2-1); (A1-58)+(S3-1); (A1-58)+(S3-2); (A1-58)+(S3-4); (A1-58)+(S3-7); (A1-58)+(S3-8); (A1-58)+(S3-10); (A1-58)+(S3-11); (A1-58)+(S4-1); (A1-58)+(S4-5); (A1-58)+(S4-6); (A1-58)+(S11-1); (A1-58)+(S11-2); (A1-58)+(S11-3); (A1-58)+(S13-1); (A1-58)+(S13-2); (A1-58)+(S13-3); (A1-58)+(S13-8); (A1-58)+(S14-1); (A1-58)+(S14-2); (A1-58)+(S14-3); (A1-59)+(S1-1); (A1-59)+(S1-7); (A1-59)+(S1-11); (A1-59)+(S2-1); (A1-59)+(S3-1); (A1-59)+(S3-2); (A1-59)+(S3-4); (A1-59)+(S3-7); (A1-59)+(S3-8); (A1-59)+(S3-10); (A1-59)+(S3-11); (A1-59)+(S4-1); (A1-59)+(S4-5); (A1-59)+(S4-6); (A1-59)+(S11-1); (A1-59)+(S11-2); (A1-59)+(S11-3); (A1-59)+(S13-1); (A1-59)+(S13-2); (A1-59)+(S13-3); (A1-59)+(S13-8); (A1-59)+(S14-1); (A1-59)+(S14-2); (A1-59)+(S14-3); (A1-60)+(S1-1); (A1-60)+(S1-7); (A1-60)+(S1-11); (A1-60)+(S2-1); (A1-60)+(S3-1); (A1-60)+(S3-2); (A1-60)+(S3-4); (A1-60)+(S3-7); (A1-60)+(S3-8); (A1-60)+(S3-10); (A1-60)+(S3-11); (A1-60)+(S4-1); (A1-60)+(S4-5); (A1-60)+(S4-6); (A1-60)+(S11-1); (A1-60)+(S11-2); (A1-60)+(S11-3); (A1-60)+(S13-1); (A1-60)+(S13-2); (A1-60)+(S13-3); (A1-60)+(S13-8); (A1-60)+(S14-1); (A1-60)+(S14-2); (A1-60)+(S14-3); (A1-61)+(S1-1); (A1-61)+(S1-7); (A1-61)+(S1-11); (A1-61)+(S2-1); (A1-61)+(S3-1); (A1-61)+(S3-2); (A1-61)+(S3-4); (A1-61)+(S3-7); (A1-61)+(S3-8); (A1-61)+(S3-10); (A1-61)+(S3-11); (A1-61)+(S4-1); (A1-61)+(S4-5); (A1-61)+(S4-6); (A1-61)+(S11-1); (A1-61)+(S11-2); (A1-61)+(S11-3); (A1-61)+(S13-1); (A1-61)+(S13-2); (A1-61)+(S13-3); (A1-61)+(S13-8); (A1-61)+(S14-1); (A1-61)+(S14-2); (A1-61)+(S14-3); (A1-62)+(S1-1); (A1-62)+(S1-7); (A1-62)+(S1-11); (A1-62)+(S2-1); (A1-62)+(S3-1); (A1-62)+(S3-2); (A1-62)+(S3-4); (A1-62)+(S3-7); (A1-62)+(S3-8); (A1-62)+(S3-10); (A1-62)+(S3-11); (A1-62)+(S4-1); (A1-62)+(S4-5); (A1-62)+(S4-6); (A1-62)+(S11-1); (A1-62)+(S11-2); (A1-62)+(S11-3); (A1-62)+(S13-1); (A1-62)+(S13-2); (A1-62)+(S13-3); (A1-62)+(S13-8); (A1-62)+(S14-1); (A1-62)+(S14-2); (A1-62)+(S14-3); (A1-63)+(S1-1); (A1-63)+(S1-7); (A1-63)+(S1-11); (A1-63)+(S2-1); (A1-63)+(S3-1); (A1-63)+(S3-2); (A1-63)+(S3-4); (A1-63)+(S3-7); (A1-63)+(S3-8); (A1-63)+(S3-10); (A1-63)+(S3-11); (A1-63)+(S4-1); (A1-63)+(S4-5); (A1-63)+(S4-6); (A1-63)+(S11-1); (A1-63)+(S11-2); (A1-63)+(S11-3); (A1-63)+(S13-1); (A1-63)+(S13-2); (A1-63)+(S13-3); (A1-63)+(S13-8); (A1-63)+(S14-1); (A1-63)+(S14-2); (A1-63)+(S14-3); (A1-64)+(S1-1); (A1-64)+(S1-7); (A1-64)+(S1-11); (A1-64)+(S2-1); (A1-64)+(S3-1); (A1-64)+(S3-2); (A1-64)+(S3-4); (A1-64)+(S3-7); (A1-64)+(S3-8); (A1-64)+(S3-10); (A1-64)+(S3-11); (A1-64)+(S4-1); (A1-64)+(S4-5); (A1-64)+(S4-6); (A1-64)+(S11-1); (A1-64)+(S11-2); (A1-64)+(S11-3); (A1-64)+(S13-1); (A1-64)+(S13-2); (A1-64)+(S13-3); (A1-64)+(S13-8); (A1-64)+(S14-1); (A1-64)+(S14-2); (A1-64)+(S14-3); (A1-65)+(S1-1); (A1-65)+(S1-7); (A1-65)+(S1-11); (A1-65)+(S2-1); (A1-65)+(S3-1); (A1-65)+(S3-2); (A1-65)+(S3-4); (A1-65)+(S3-7); (A1-65)+(S3-8); (A1-65)+(S3-10); (A1-65)+(S3-11); (A1-65)+(S4-1); (A1-65)+(S4-5); (A1-65)+(S4-6); (A1-65)+(S11-1); (A1-65)+(S11-2); (A1-65)+(S11-3); (A1-65)+(S13-1); (A1-65)+(S13-2); (A1-65)+(S13-3); (A1-65)+(S13-8); (A1-65)+(S14-1); (A1-65)+(S14-2); (A1-65)+(S14-3); (A1-66)+(S1-1); (A1-66)+(S1-7); (A1-66)+(S1-11); (A1-66)+(S2-1); (A1-66)+(S3-1); (A1-66)+(S3-2); (A1-66)+(S3-4); (A1-66)+(S3-7); (A1-66)+(S3-8); (A1-66)+(S3-10); (A1-66)+(S3-11); (A1-66)+(S4-1); (A1-66)+(S4-5); (A1-66)+(S4-6); (A1-66)+(S11-1); (A1-66)+(S11-2); (A1-66)+(S11-3); (A1-66)+(S13-1); (A1-66)+(S13-2); (A1-66)+(S13-3); (A1-66)+(S13-8); (A1-66)+(S14-1); (A1-66)+(S14-2); (A1-66)+(S14-3); (A1-67)+(S1-1); (A1-67)+(S1-7); (A1-67)+(S1-11); (A1-67)+(S2-1); (A1-67)+(S3-1); (A1-67)+(S3-2); (A1-67)+(S3-4); (A1-67)+(S3-7); (A1-67)+(S3-8); (A1-67)+(S3-10); (A1-67)+(S3-11); (A1-67)+(S4-1); (A1-67)+(S4-5); (A1-67)+(S4-6); (A1-67)+(S11-1); (A1-67)+(S11-2); (A1-67)+(S11-3); (A1-67)+(S13-1); (A1-67)+(S13-2); (A1-67)+(S13-3); (A1-67)+(S13-8); (A1-67)+(S14-1); (A1-67)+(S14-2); (A1-67)+(S14-3); (A1-68)+(S1-1); (A1-68)+(S1-7); (A1-68)+(S1-11); (A1-68)+(S2-1); (A1-68)+(S3-1); (A1-68)+(S3-2); (A1-68)+(S3-4); (A1-68)+(S3-7); (A1-68)+(S3-8); (A1-68)+(S3-10); (A1-68)+(S3-11); (A1-68)+(S4-1); (A1-68)+(S4-5); (A1-68)+(S4-6); (A1-68)+(S11-1); (A1-68)+(S11-2); (A1-68)+(S11-3); (A1-68)+(S13-1); (A1-68)+(S13-2); (A1-68)+(S13-3); (A1-68)+(S13-8); (A1-68)+(S14-1); (A1-68)+(S14-2); (A1-68)+(S14-3); (A1-69)+(S1-1); (A1-69)+(S1-7); (A1-69)+(S1-11); (A1-69)+(S2-1); (A1-69)+(S3-1); (A1-69)+(S3-2); (A1-69)+(S3-4); (A1-69)+(S3-7); (A1-69)+(S3-8); (A1-69)+(S3-10); (A1-69)+(S3-11); (A1-69)+(S4-1); (A1-69)+(S4-5); (A1-69)+(S4-6); (A1-69)+(S11-1); (A1-69)+(S11-2); (A1-69)+(S11-3); (A1-69)+(S13-1); (A1-69)+(S13-2); (A1-69)+(S13-3); (A1-69)+(S13-8); (A1-69)+(S14-1); (A1-69)+(S14-2); (A1-69)+(S14-3); (A1-70)+(S1-1); (A1-70)+(S1-7); (A1-70)+(S1-11); (A1-70)+(S2-1); (A1-70)+(S3-1); (A1-70)+(S3-2); (A1-70)+(S3-4); (A1-70)+(S3-7); (A1-70)+(S3-8); (A1-70)+(S3-10); (A1-70)+(S3-11); (A1-70)+(S4-1); (A1-70)+(S4-5); (A1-70)+(S4-6); (A1-70)+(S11-1); (A1-70)+(S11-2); (A1-70)+(S11-3); (A1-70)+(S13-1); (A1-70)+(S13-2); (A1-70)+(S13-3); (A1-70)+(S13-8); (A1-70)+(S14-1); (A1-70)+(S14-2); (A1-70)+(S14-3); (A1-71)+(S1-1); (A1-71)+(S1-7); (A1-71)+(S1-11); (A1-71)+(S2-1); (A1-71)+(S3-1); (A1-71)+(S3-2); (A1-71)+(S3-4); (A1-71)+(S3-7); (A1-71)+(S3-8); (A1-71)+(S3-10); (A1-71)+(S3-11); (A1-71)+(S4-1); (A1-71)+(S4-5); (A1-71)+(S4-6); (A1-71)+(S11-1); (A1-71)+(S11-2); (A1-71)+(S11-3); (A1-71)+(S13-1); (A1-71)+(S13-2); (A1-71)+(S13-3); (A1-71)+(S13-8); (A1-71)+(S14-1); (A1-71)+(S14-2); (A1-71)+(S14-3); (A1-72)+(S1-1); (A1-72)+(S1-7); (A1-72)+(S1-11); (A1-72)+(S2-1); (A1-72)+(S3-1); (A1-72)+(S3-2); (A1-72)+(S3-4); (A1-72)+(S3-7); (A1-72)+(S3-8); (A1-72)+(S3-10); (A1-72)+(S3-11); (A1-72)+(S4-1); (A1-72)+(S4-5); (A1-72)+(S4-6); (A1-72)+(S11-1); (A1-72)+(S11-2); (A1-72)+(S11-3); (A1-72)+(S13-1); (A1-72)+(S13-2); (A1-72)+(S13-3); (A1-72)+(S13-8); (A1-72)+(S14-1); (A1-72)+(S14-2); (A1-72)+(S14-3); (A1-73)+(S1-1); (A1-73)+(S1-7); (A1-73)+(S1-11); (A1-73)+(S2-1); (A1-73)+(S3-1); (A1-73)+(S3-2); (A1-73)+(S3-4); (A1-73)+(S3-7); (A1-73)+(S3-8); (A1-73)+(S3-10); (A1-73)+(S3-11); (A1-73)+(S4-1); (A1-73)+(S4-5); (A1-73)+(S4-6); (A1-73)+(S11-1); (A1-73)+(S11-

2); (A1-73)+(S11-3); (A1-73)+(S13-1); (A1-73)+(S13-2); (A1-73)+(S13-3); (A1-73)+(S13-8); (A1-73)+(S14-1); (A1-73)+(S14-2); (A1-73)+(S14-3); (A1-74)+(S1-1); (A1-74)+(S1-7); (A1-74)+(S1-11); (A1-74)+(S2-1); (A1-74)+(S3-1); (A1-74)+(S3-2); (A1-74)+(S3-4); (A1-74)+(S3-7); (A1-74)+(S3-8); (A1-74)+(S3-10); (A1-74)+(S3-11); (A1-74)+(S4-1); (A1-74)+(S4-5); (A1-74)+(S4-6); (A1-74)+(S11-1); (A1-74)+(S11-2); (A1-74)+(S11-3); (A1-74)+(S13-1); (A1-74)+(S13-2); (A1-74)+(S13-3); (A1-74)+(S13-8); (A1-74)+(S14-1); (A1-74)+(S14-2); (A1-74)+(S14-3); (A1-75)+(S1-1); (A1-75)+(S1-7); (A1-75)+(S1-11); (A1-75)+(S2-1); (A1-75)+(S3-1); (A1-75)+(S3-2); (A1-75)+(S3-4); (A1-75)+(S3-7); (A1-75)+(S3-8); (A1-75)+(S3-10); (A1-75)+(S3-11); (A1-75)+(S4-1); (A1-75)+(S4-5); (A1-75)+(S4-6); (A1-75)+(S11-1); (A1-75)+(S11-2); (A1-75)+(S11-3); (A1-75)+(S13-1); (A1-75)+(S13-2); (A1-75)+(S13-3); (A1-75)+(S13-8); (A1-75)+(S14-1); (A1-75)+(S14-2); (A1-75)+(S14-3); (A1-76)+(S1-1); (A1-76)+(S1-7); (A1-76)+(S1-11); (A1-76)+(S2-1); (A1-76)+(S3-1); (A1-76)+(S3-2); (A1-76)+(S3-4); (A1-76)+(S3-7); (A1-76)+(S3-8); (A1-76)+(S3-10); (A1-76)+(S3-11); (A1-76)+(S4-1); (A1-76)+(S4-5); (A1-76)+(S4-6); (A1-76)+(S11-1); (A1-76)+(S11-2); (A1-76)+(S11-3); (A1-76)+(S13-1); (A1-76)+(S13-2); (A1-76)+(S13-3); (A1-76)+(S13-8); (A1-76)+(S14-1); (A1-76)+(S14-2); (A1-76)+(S14-3); (A1-77)+(S1-1); (A1-77)+(S1-7); (A1-77)+(S1-11); (A1-77)+(S2-1); (A1-77)+(S3-1); (A1-77)+(S3-2); (A1-77)+(S3-4); (A1-77)+(S3-7); (A1-77)+(S3-8); (A1-77)+(S3-10); (A1-77)+(S3-11); (A1-77)+(S4-1); (A1-77)+(S4-5); (A1-77)+(S4-6); (A1-77)+(S11-1); (A1-77)+(S11-2); (A1-77)+(S11-3); (A1-77)+(S13-1); (A1-77)+(S13-2); (A1-77)+(S13-3); (A1-77)+(S13-8); (A1-77)+(S14-1); (A1-77)+(S14-2); (A1-77)+(S14-3); (A1-78)+(S1-1); (A1-78)+(S1-7); (A1-78)+(S1-11); (A1-78)+(S2-1); (A1-78)+(S3-1); (A1-78)+(S3-2); (A1-78)+(S3-4); (A1-78)+(S3-7); (A1-78)+(S3-8); (A1-78)+(S3-10); (A1-78)+(S3-11); (A1-78)+(S4-1); (A1-78)+(S4-5); (A1-78)+(S4-6); (A1-78)+(S11-1); (A1-78)+(S11-2); (A1-78)+(S11-3); (A1-78)+(S13-1); (A1-78)+(S13-2); (A1-78)+(S13-3); (A1-78)+(S13-8); (A1-78)+(S14-1); (A1-78)+(S14-2); (A1-78)+(S14-3); (A1-79)+(S1-1); (A1-79)+(S1-7); (A1-79)+(S1-11); (A1-79)+(S2-1); (A1-79)+(S3-1); (A1-79)+(S3-2); (A1-79)+(S3-4); (A1-79)+(S3-7); (A1-79)+(S3-8); (A1-79)+(S3-10); (A1-79)+(S3-11); (A1-79)+(S4-1); (A1-79)+(S4-5); (A1-79)+(S4-6); (A1-79)+(S11-1); (A1-79)+(S11-2); (A1-79)+(S11-3); (A1-79)+(S13-1); (A1-79)+(S13-2); (A1-79)+(S13-3); (A1-79)+(S13-8); (A1-79)+(S14-1); (A1-79)+(S14-2); (A1-79)+(S14-3); (A1-80)+(S1-1); (A1-80)+(S1-7); (A1-80)+(S1-11); (A1-80)+(S2-1); (A1-80)+(S3-1); (A1-80)+(S3-2); (A1-80)+(S3-4); (A1-80)+(S3-7); (A1-80)+(S3-8); (A1-80)+(S3-10); (A1-80)+(S3-11); (A1-80)+(S4-1); (A1-80)+(S4-5); (A1-80)+(S4-6); (A1-80)+(S11-1); (A1-80)+(S11-2); (A1-80)+(S11-3); (A1-80)+(S13-1); (A1-80)+(S13-2); (A1-80)+(S13-3); (A1-80)+(S13-8); (A1-80)+(S14-1); (A1-80)+(S14-2); (A1-80)+(S14-3); (A1-81)+(S1-1); (A1-81)+(S1-7); (A1-81)+(S1-11); (A1-81)+(S2-1); (A1-81)+(S3-1); (A1-81)+(S3-2); (A1-81)+(S3-4); (A1-81)+(S3-7); (A1-81)+(S3-8); (A1-81)+(S3-10); (A1-81)+(S3-11); (A1-81)+(S4-1); (A1-81)+(S4-5); (A1-81)+(S4-6); (A1-81)+(S11-1); (A1-81)+(S11-2); (A1-81)+(S11-3); (A1-81)+(S13-1); (A1-81)+(S13-2); (A1-81)+(S13-3); (A1-81)+(S13-8); (A1-81)+(S14-1); (A1-81)+(S14-2); (A1-81)+(S14-3); (A1-82)+(S1-1); (A1-82)+(S1-7); (A1-82)+(S1-11); (A1-82)+(S2-1); (A1-82)+(S3-1); (A1-82)+(S3-2); (A1-82)+(S3-4); (A1-82)+(S3-7); (A1-82)+(S3-8); (A1-82)+(S3-10); (A1-82)+(S3-11); (A1-82)+(S4-1); (A1-82)+(S4-5); (A1-82)+(S4-6); (A1-82)+(S11-1); (A1-82)+(S11-2); (A1-82)+(S11-3); (A1-82)+(S13-1); (A1-82)+(S13-2); (A1-82)+(S13-3); (A1-82)+(S13-8); (A1-82)+(S14-1); (A1-82)+(S14-2); (A1-82)+(S14-3); (A1-83)+(S1-1); (A1-83)+(S1-7); (A1-83)+(S1-11); (A1-83)+(S2-1); (A1-83)+(S3-1); (A1-83)+(S3-2); (A1-83)+(S3-4); (A1-83)+(S3-7); (A1-83)+(S3-8); (A1-83)+(S3-10); (A1-83)+(S3-11); (A1-83)+(S4-1); (A1-83)+(S4-5); (A1-83)+(S4-6); (A1-83)+(S11-1); (A1-83)+(S11-2); (A1-83)+(S11-3); (A1-83)+(S13-1); (A1-83)+(S13-2); (A1-83)+(S13-3); (A1-83)+(S13-8); (A1-83)+(S14-1); (A1-83)+(S14-2); (A1-83)+(S14-3); (A1-84)+(S1-1); (A1-84)+(S1-7); (A1-84)+(S1-11); (A1-84)+(S2-1); (A1-84)+(S3-1); (A1-84)+(S3-2); (A1-84)+(S3-4); (A1-84)+(S3-7); (A1-84)+(S3-8); (A1-84)+(S3-10); (A1-84)+(S3-11); (A1-84)+(S4-1); (A1-84)+(S4-5); (A1-84)+(S4-6); (A1-84)+(S11-1); (A1-84)+(S11-2); (A1-84)+(S11-3); (A1-84)+(S13-1); (A1-84)+(S13-2); (A1-84)+(S13-3); (A1-84)+(S13-8); (A1-84)+(S14-1); (A1-84)+(S14-2); (A1-84)+(S14-3); (A1-85)+(S1-1); (A1-85)+(S1-7); (A1-85)+(S1-11); (A1-85)+(S2-1); (A1-85)+(S3-1); (A1-85)+(S3-2); (A1-85)+(S3-4); (A1-85)+(S3-7); (A1-85)+(S3-8); (A1-85)+(S3-10); (A1-85)+(S3-11); (A1-85)+(S4-1); (A1-85)+(S4-5); (A1-85)+(S4-6); (A1-85)+(S11-1); (A1-85)+(S11-2); (A1-85)+(S11-3); (A1-85)+(S13-1); (A1-85)+(S13-2); (A1-85)+(S13-3); (A1-85)+(S13-8); (A1-85)+(S14-1); (A1-85)+(S14-2); (A1-85)+(S14-3); (A1-86)+(S1-1); (A1-86)+(S1-7); (A1-86)+(S1-11); (A1-86)+(S2-1); (A1-86)+(S3-1); (A1-86)+(S3-2); (A1-86)+(S3-4); (A1-86)+(S3-7); (A1-86)+(S3-8); (A1-86)+(S3-10); (A1-86)+(S3-11); (A1-86)+(S4-1); (A1-86)+(S4-5); (A1-86)+(S4-6); (A1-86)+(S11-1); (A1-86)+(S11-2); (A1-86)+(S11-3); (A1-86)+(S13-1); (A1-86)+(S13-2); (A1-86)+(S13-3); (A1-86)+(S13-8); (A1-86)+(S14-1); (A1-86)+(S14-2); (A1-86)+(S14-3); (A1-87)+(S1-1); (A1-87)+(S1-7); (A1-87)+(S1-11); (A1-87)+(S2-1); (A1-87)+(S3-1); (A1-87)+(S3-2); (A1-87)+(S3-4); (A1-87)+(S3-7); (A1-87)+(S3-8); (A1-87)+(S3-10); (A1-87)+(S3-11); (A1-87)+(S4-1); (A1-87)+(S4-5); (A1-87)+(S4-6); (A1-87)+(S11-1); (A1-87)+(S11-2); (A1-87)+(S11-3); (A1-87)+(S13-1); (A1-87)+(S13-2); (A1-87)+(S13-3); (A1-87)+(S13-8); (A1-87)+(S14-1); (A1-87)+(S14-2); (A1-87)+(S14-3); (A1-88)+(S1-1); (A1-88)+(S1-7); (A1-88)+(S1-11); (A1-88)+(S2-1); (A1-88)+(S3-1); (A1-88)+(S3-2); (A1-88)+(S3-4); (A1-88)+(S3-7); (A1-88)+(S3-8); (A1-88)+(S3-10); (A1-88)+(S3-11); (A1-88)+(S4-1); (A1-88)+(S4-5); (A1-88)+(S4-6); (A1-88)+(S11-1); (A1-88)+(S11-2); (A1-88)+(S11-3); (A1-88)+(S13-1); (A1-88)+(S13-2); (A1-88)+(S13-3); (A1-88)+(S13-8); (A1-88)+(S14-1); (A1-88)+(S14-2); (A1-88)+(S14-3); (A1-89)+(S1-1); (A1-89)+(S1-7); (A1-89)+(S1-11); (A1-89)+(S2-1); (A1-89)+(S3-1); (A1-89)+(S3-2); (A1-89)+(S3-4); (A1-89)+(S3-7); (A1-89)+(S3-8); (A1-89)+(S3-10); (A1-89)+(S3-11); (A1-89)+(S4-1); (A1-89)+(S4-5); (A1-89)+(S4-6); (A1-89)+(S11-1); (A1-89)+(S11-2); (A1-89)+(S11-3); (A1-89)+(S13-1); (A1-89)+(S13-2); (A1-89)+(S13-3); (A1-89)+(S13-8); (A1-89)+(S14-1); (A1-89)+(S14-2); (A1-89)+(S14-3); (A1-90)+(S1-1); (A1-90)+(S1-7); (A1-90)+(S1-11); (A1-90)+(S2-1); (A1-90)+(S3-1); (A1-90)+(S3-2); (A1-90)+(S3-4); (A1-90)+(S3-7); (A1-90)+(S3-8); (A1-90)+(S3-10); (A1-90)+(S3-11); (A1-90)+(S4-1); (A1-90)+(S4-5); (A1-90)+(S4-6); (A1-90)+(S11-1); (A1-90)+(S11-2); (A1-90)+(S11-3); (A1-90)+(S13-1); (A1-90)+(S13-2); (A1-90)+(S13-3); (A1-90)+(S13-8); (A1-90)+(S14-1); (A1-90)+(S14-2); (A1-90)+(S14-3); (A1-91)+(S1-1); (A1-91)+(S1-7); (A1-91)+(S1-11); (A1-91)+(S2-1); (A1-91)+(S3-1); (A1-91)+(S3-2); (A1-91)+(S3-4); (A1-91)+(S3-7); (A1-91)+(S3-8); (A1-91)+(S3-10); (A1-91)+(S3-11); (A1-91)+(S4-1); (A1-91)+(S4-5); (A1-91)+(S4-6); (A1-91)+(S11-1); (A1-91)+(S11-2); (A1-91)+(S11-3); (A1-91)+(S13-1); (A1-91)+(S13-2); (A1-91)+(S13-3); (A1-91)+(S13-8); (A1-91)+(S14-1); (A1-91)+(S14-2); (A1-91)+(S14-3); (A1-92)+(S1-1); (A1-92)+(S1-7); (A1-92)+(S1-11); (A1-

92)+(S2-1); (A1-92)+(S3-1); (A1-92)+(S3-4); (A1-92)+(S3-7); (A1-92)+(S3-8); (A1-92)+(S3-10); (A1-92)+(S3-11); (A1-92)+(S4-1); (A1-92)+(S4-5); (A1-92)+(S4-6); (A1-92)+(S11-1); (A1-92)+(S11-2); (A1-92)+(S11-3); (A1-92)+(S13-1); (A1-92)+(S13-2); (A1-92)+(S13-3); (A1-92)+(S13-8); (A1-92)+(S14-1); (A1-92)+(S14-2); (A1-92)+(S14-3); (A1-93)+(S1-1); (A1-93)+(S1-7); (A1-93)+(S1-11); (A1-93)+(S2-1); (A1-93)+(S3-1); (A1-93)+(S3-2); (A1-93)+(S3-4); (A1-93)+(S3-7); (A1-93)+(S3-8); (A1-93)+(S3-10); (A1-93)+(S3-11); (A1-93)+(S4-1); (A1-93)+(S4-5); (A1-93)+(S4-6); (A1-93)+(S11-1); (A1-93)+(S11-2); (A1-93)+(S11-3); (A1-93)+(S13-1); (A1-93)+(S13-2); (A1-93)+(S13-3); (A1-93)+(S13-8); (A1-93)+(S14-1); (A1-93)+(S14-2); (A1-93)+(S14-3); (A1-94)+(S1-1); (A1-94)+(S1-7); (A1-94)+(S1-11); (A1-94)+(S2-1); (A1-94)+(S3-1); (A1-94)+(S3-2); (A1-94)+(S3-4); (A1-94)+(S3-7); (A1-94)+(S3-8); (A1-94)+(S3-10); (A1-94)+(S3-11); (A1-94)+(S4-1); (A1-94)+(S4-5); (A1-94)+(S4-6); (A1-94)+(S11-1); (A1-94)+(S11-2); (A1-94)+(S11-3); (A1-94)+(S13-1); (A1-94)+(S13-2); (A1-94)+(S13-3); (A1-94)+(S13-8); (A1-94)+(S14-1); (A1-94)+(S14-2); (A1-94)+(S14-3); (A1-95)+(S1-1); (A1-95)+(S1-7); (A1-95)+(S1-11); (A1-95)+(S2-1); (A1-95)+(S3-1); (A1-95)+(S3-2); (A1-95)+(S3-4); (A1-95)+(S3-7); (A1-95)+(S3-8); (A1-95)+(S3-10); (A1-95)+(S3-11); (A1-95)+(S4-1); (A1-95)+(S4-5); (A1-95)+(S4-6); (A1-95)+(S11-1); (A1-95)+(S11-2); (A1-95)+(S11-3); (A1-95)+(S13-1); (A1-95)+(S13-2); (A1-95)+(S13-3); (A1-95)+(S13-8); (A1-95)+(S14-1); (A1-95)+(S14-2); (A1-95)+(S14-3); (A1-96)+(S1-1); (A1-96)+(S1-7); (A1-96)+(S1-11); (A1-96)+(S2-1); (A1-96)+(S3-1); (A1-96)+(S3-2); (A1-96)+(S3-4); (A1-96)+(S3-7); (A1-96)+(S3-8); (A1-96)+(S3-10); (A1-96)+(S3-11); (A1-96)+(S4-1); (A1-96)+(S4-5); (A1-96)+(S4-6); (A1-96)+(S11-1); (A1-96)+(S11-2); (A1-96)+(S11-3); (A1-96)+(S13-1); (A1-96)+(S13-2); (A1-96)+(S13-3); (A1-96)+(S13-8); (A1-96)+(S14-1); (A1-96)+(S14-2); (A1-96)+(S14-3); (A1-97)+(S1-1); (A1-97)+(S1-7); (A1-97)+(S1-11); (A1-97)+(S2-1); (A1-97)+(S3-1); (A1-97)+(S3-2); (A1-97)+(S3-4); (A1-97)+(S3-7); (A1-97)+(S3-8); (A1-97)+(S3-10); (A1-97)+(S3-11); (A1-97)+(S4-1); (A1-97)+(S4-5); (A1-97)+(S4-6); (A1-97)+(S11-1); (A1-97)+(S11-2); (A1-97)+(S11-3); (A1-97)+(S13-1); (A1-97)+(S13-2); (A1-97)+(S13-3); (A1-97)+(S13-8); (A1-97)+(S14-1); (A1-97)+(S14-2); (A1-97)+(S14-3); (A1-98)+(S1-1); (A1-98)+(S1-7); (A1-98)+(S1-11); (A1-98)+(S2-1); (A1-98)+(S3-1); (A1-98)+(S3-2); (A1-98)+(S3-4); (A1-98)+(S3-7); (A1-98)+(S3-8); (A1-98)+(S3-10); (A1-98)+(S3-11); (A1-98)+(S4-1); (A1-98)+(S4-5); (A1-98)+(S4-6); (A1-98)+(S11-1); (A1-98)+(S11-2); (A1-98)+(S11-3); (A1-98)+(S13-1); (A1-98)+(S13-2); (A1-98)+(S13-3); (A1-98)+(S13-8); (A1-98)+(S14-1); (A1-98)+(S14-2); (A1-98)+(S14-3); (A1-99)+(S1-1); (A1-99)+(S1-7); (A1-99)+(S1-11); (A1-99)+(S2-1); (A1-99)+(S3-1); (A1-99)+(S3-2); (A1-99)+(S3-4); (A1-99)+(S3-7); (A1-99)+(S3-8); (A1-99)+(S3-10); (A1-99)+(S3-11); (A1-99)+(S4-1); (A1-99)+(S4-5); (A1-99)+(S4-6); (A1-99)+(S11-1); (A1-99)+(S11-2); (A1-99)+(S11-3); (A1-99)+(S13-1); (A1-99)+(S13-2); (A1-99)+(S13-3); (A1-99)+(S13-8); (A1-99)+(S14-1); (A1-99)+(S14-2); (A1-99)+(S14-3); (A1-100)+(S1-1); (A1-100)+(S1-7); (A1-100)+(S1-11); (A1-100)+(S2-1); (A1-100)+(S3-1); (A1-100)+(S3-2); (A1-100)+(S3-4); (A1-100)+(S3-7); (A1-100)+(S3-8); (A1-100)+(S3-10); (A1-100)+(S3-11); (A1-100)+(S4-1); (A1-100)+(S4-5); (A1-100)+(S4-6); (A1-100)+(S11-1); (A1-100)+(S11-2); (A1-100)+(S11-3); (A1-100)+(S13-1); (A1-100)+(S13-2); (A1-100)+(S13-3); (A1-100)+(S13-8); (A1-100)+(S14-1); (A1-100)+(S14-2); (A1-100)+(S14-3); (A1-101)+(S1-1); (A1-101)+(S1-7); (A1-101)+(S1-11); (A1-101)+(S2-1); (A1-101)+(S3-1); (A1-101)+(S3-2); (A1-101)+(S3-4); (A1-101)+(S3-7); (A1-101)+(S3-8); (A1-101)+(S3-10); (A1-101)+(S3-11); (A1-101)+(S4-1); (A1-101)+(S4-5); (A1-101)+(S4-6); (A1-101)+(S11-1); (A1-101)+(S11-2); (A1-101)+(S11-3); (A1-101)+(S13-1); (A1-101)+(S13-2); (A1-101)+(S13-3); (A1-101)+(S13-8); (A1-101)+(S14-1); (A1-101)+(S14-2); (A1-101)+(S14-3); (A1-102)+(S1-1); (A1-102)+(S1-7); (A1-102)+(S1-11); (A1-102)+(S2-1); (A1-102)+(S3-1); (A1-102)+(S3-2); (A1-102)+(S3-4); (A1-102)+(S3-7); (A1-102)+(S3-8); (A1-102)+(S3-10); (A1-102)+(S3-11); (A1-102)+(S4-1); (A1-102)+(S4-5); (A1-102)+(S4-6); (A1-102)+(S11-1); (A1-102)+(S11-2); (A1-102)+(S11-3); (A1-102)+(S13-1); (A1-102)+(S13-2); (A1-102)+(S13-3); (A1-102)+(S13-8); (A1-102)+(S14-1); (A1-102)+(S14-2); (A1-102)+(S14-3); (A1-103)+(S1-1); (A1-103)+(S1-7); (A1-103)+(S1-11); (A1-103)+(S2-1); (A1-103)+(S3-1); (A1-103)+(S3-2); (A1-103)+(S3-4); (A1-103)+(S3-7); (A1-103)+(S3-8); (A1-103)+(S3-10); (A1-103)+(S3-11); (A1-103)+(S4-1); (A1-103)+(S4-5); (A1-103)+(S4-6); (A1-103)+(S11-1); (A1-103)+(S11-2); (A1-103)+(S11-3); (A1-103)+(S13-1); (A1-103)+(S13-2); (A1-103)+(S13-3); (A1-103)+(S13-8); (A1-103)+(S14-1); (A1-103)+(S14-2); (A1-103)+(S14-3); (A1-104)+(S1-1); (A1-104)+(S1-7); (A1-104)+(S1-11); (A1-104)+(S2-1); (A1-104)+(S3-1); (A1-104)+(S3-2); (A1-104)+(S3-4); (A1-104)+(S3-7); (A1-104)+(S3-8); (A1-104)+(S3-10); (A1-104)+(S3-11); (A1-104)+(S4-1); (A1-104)+(S4-5); (A1-104)+(S4-6); (A1-104)+(S11-1); (A1-104)+(S11-2); (A1-104)+(S11-3); (A1-104)+(S13-1); (A1-104)+(S13-2); (A1-104)+(S13-3); (A1-104)+(S13-8); (A1-104)+(S14-1); (A1-104)+(S14-2); (A1-104)+(S14-3); (A1-105)+(S1-1); (A1-105)+(S1-7); (A1-105)+(S1-11); (A1-105)+(S2-1); (A1-105)+(S3-1); (A1-105)+(S3-2); (A1-105)+(S3-4); (A1-105)+(S3-7); (A1-105)+(S3-8); (A1-105)+(S3-10); (A1-105)+(S3-11); (A1-105)+(S4-1); (A1-105)+(S4-5); (A1-105)+(S4-6); (A1-105)+(S11-1); (A1-105)+(S11-2); (A1-105)+(S11-3); (A1-105)+(S13-1); (A1-105)+(S13-2); (A1-105)+(S13-3); (A1-105)+(S13-8); (A1-105)+(S14-1); (A1-105)+(S14-2); (A1-105)+(S14-3); (A1-106)+(S1-1); (A1-106)+(S1-7); (A1-106)+(S1-11); (A1-106)+(S2-1); (A1-106)+(S3-1); (A1-106)+(S3-2); (A1-106)+(S3-4); (A1-106)+(S3-7); (A1-106)+(S3-8); (A1-106)+(S3-10); (A1-106)+(S3-11); (A1-106)+(S4-1); (A1-106)+(S4-5); (A1-106)+(S4-6); (A1-106)+(S11-1); (A1-106)+(S11-2); (A1-106)+(S11-3); (A1-106)+(S13-1); (A1-106)+(S13-2); (A1-106)+(S13-3); (A1-106)+(S13-8); (A1-106)+(S14-1); (A1-106)+(S14-2); (A1-106)+(S14-3); (A2-1)+(S1-1); (A2-1)+(S1-7); (A2-1)+(S1-11); (A2-1)+(S2-1); (A2-1)+(S3-1); (A2-1)+(S3-2); (A2-1)+(S3-4); (A2-1)+(S3-7); (A2-1)+(S3-8); (A2-1)+(S3-10); (A2-1)+(S3-11); (A2-1)+(S4-1); (A2-1)+(S4-5); (A2-1)+(S4-6); (A2-1)+(S11-1); (A2-1)+(S11-2); (A2-1)+(S11-3); (A2-1)+(S13-1); (A2-1)+(S13-2); (A2-1)+(S13-3); (A2-1)+(S13-8); (A2-1)+(S14-1); (A2-1)+(S14-2); (A2-1)+(S14-3); (A2-2)+(S1-1); (A2-2)+(S1-7); (A2-2)+(S1-11); (A2-2)+(S2-1); (A2-2)+(S3-1); (A2-2)+(S3-2); (A2-2)+(S3-4); (A2-2)+(S3-7); (A2-2)+(S3-8); (A2-2)+(S3-10); (A2-2)+(S3-11); (A2-2)+(S4-1); (A2-2)+(S4-5); (A2-2)+(S4-6); (A2-2)+(S11-1); (A2-2)+(S11-2); (A2-2)+(S11-3); (A2-2)+(S13-1); (A2-2)+(S13-2); (A2-2)+(S13-3); (A2-2)+(S13-8); (A2-2)+(S14-1); (A2-2)+(S14-2); (A2-2)+(S14-3); (A2-3)+(S1-1); (A2-3)+(S1-7); (A2-3)+(S1-11); (A2-3)+(S2-1); (A2-3)+(S3-1); (A2- 3)+(S3-2); (A2-3)+(S3-4); (A2-3)+(S3-7); (A2-3)+(S3-8); (A2-3)+(S3-10); (A2-3)+(S3-11); (A2-3)+(S4-1); (A2-3)+(S4-5); (A2-3)+(S4-6); (A2-3)+(S11-1); (A2-3)+(S11-2); (A2-3)+(S11-3); (A2-3)+(S13-1); (A2-3)+(S13-2); (A2-3)+(S13-3); (A2-3)+(S13-8); (A2-3)+(S14-1); (A2-3)+(S14-2); (A2-3)+(S14-3); (A2-4)+(S1-1); (A2-4)+(S1-7); (A2-4)+(S1-11); (A2-4)+

(S2-1); (A2-4)+(S3-1); (A2-4)+(S3-2); (A2-4)+(S3-4); (A2-4)+(S3-7); (A2-4)+(S3-8); (A2-4)+(S3-10); (A2-4)+(S3-11); (A2-4)+(S4-1); (A2-4)+(S4-5); (A2-4)+(S4-6); (A2-4)+(S11-1); (A2-4)+(S11-2); (A2-4)+(S11-3); (A2-4)+(S13-1); (A2-4)+(S13-2); (A2-4)+(S13-3); (A2-4)+(S13-8); (A2-4)+(S14-1); (A2-4)+(S14-2); (A2-4)+(S14-3); (A2-5)+(S1-1); (A2-5)+(S1-7); (A2-5)+(S1-11); (A2-5)+(S2-1); (A2-5)+(S3-1); (A2-5)+(S3-2); (A2-5)+(S3-4); (A2-5)+(S3-7); (A2-5)+(S3-8); (A2-5)+(S3-10); (A2-5)+(S3-11); (A2-5)+(S4-1); (A2-5)+(S4-5); (A2-5)+(S4-6); (A2-5)+(S11-1); (A2-5)+(S11-2); (A2-5)+(S11-3); (A2-5)+(S13-1); (A2-5)+(S13-2); (A2-5)+(S13-3); (A2-5)+(S13-8); (A2-5)+(S14-1); (A2-5)+(S14-2); (A2-5)+(S14-3); (A2-6)+(S1-1); (A2-6)+(S1-7); (A2-6)+(S1-11); (A2-6)+(S2-1); (A2-6)+(S3-1); (A2-6)+(S3-2); (A2-6)+(S3-4); (A2-6)+(S3-7); (A2-6)+(S3-8); (A2-6)+(S3-10); (A2-6)+(S3-11); (A2-6)+(S4-1); (A2-6)+(S4-5); (A2-6)+(S4-6); (A2-6)+(S11-1); (A2-6)+(S11-2); (A2-6)+(S11-3); (A2-6)+(S13-1); (A2-6)+(S13-2); (A2-6)+(S13-3); (A2-6)+(S13-8); (A2-6)+(S14-1); (A2-6)+(S14-2); (A2-6)+(S14-3); (A2-7)+(S1-1); (A2-7)+(S1-7); (A2-7)+(S1-11); (A2-7)+(S2-1); (A2-7)+(S3-1); (A2-7)+(S3-2); (A2-7)+(S3-4); (A2-7)+(S3-7); (A2-7)+(S3-8); (A2-7)+(S3-10); (A2-7)+(S3-11); (A2-7)+(S4-1); (A2-7)+(S4-5); (A2-7)+(S4-6); (A2-7)+(S11-1); (A2-7)+(S11-2); (A2-7)+(S11-3); (A2-7)+(S13-1); (A2-7)+(S13-2); (A2-7)+(S13-3); (A2-7)+(S13-8); (A2-7)+(S14-1); (A2-7)+(S14-2); (A2-7)+(S14-3); (A2-8)+(S1-1); (A2-8)+(S1-7); (A2-8)+(S1-11); (A2-8)+(S2-1); (A2-8)+(S3-1); (A2-8)+(S3-2); (A2-8)+(S3-4); (A2-8)+(S3-7); (A2-8)+(S3-8); (A2-8)+(S3-10); (A2-8)+(S3-11); (A2-8)+(S4-1); (A2-8)+(S4-5); (A2-8)+(S4-6); (A2-8)+(S11-1); (A2-8)+(S11-2); (A2-8)+(S11-3); (A2-8)+(S13-1); (A2-8)+(S13-2); (A2-8)+(S13-3); (A2-8)+(S13-8); (A2-8)+(S14-1); (A2-8)+(S14-2); (A2-8)+(S14-3); (A2-9)+(S1-1); (A2-9)+(S1-7); (A2-9)+(S1-11); (A2-9)+(S2-1); (A2-9)+(S3-1); (A2-9)+(S3-2); (A2-9)+(S3-4); (A2-9)+(S3-7); (A2-9)+(S3-8); (A2-9)+(S3-10); (A2-9)+(S3-11); (A2-9)+(S4-1); (A2-9)+(S4-5); (A2-9)+(S4-6); (A2-9)+(S11-1); (A2-9)+(S11-2); (A2-9)+(S11-3); (A2-9)+(S13-1); (A2-9)+(S13-2); (A2-9)+(S13-3); (A2-9)+(S13-8); (A2-9)+(S14-1); (A2-9)+(S14-2); (A2-9)+(S14-3); (A2-10)+(S1-1); (A2-10)+(S1-7); (A2-10)+(S1-11); (A2-10)+(S2-1); (A2-10)+(S3-1); (A2-10)+(S3-2); (A2-10)+(S3-4); (A2-10)+(S3-7); (A2-10)+(S3-8); (A2-10)+(S3-10); (A2-10)+(S3-11); (A2-10)+(S4-1); (A2-10)+(S4-5); (A2-10)+(S4-6); (A2-10)+(S11-1); (A2-10)+(S11-2); (A2-10)+(S11-3); (A2-10)+(S13-1); (A2-10)+(S13-2); (A2-10)+(S13-3); (A2-10)+(S13-8); (A2-10)+(S14-1); (A2-10)+(S14-2); (A2-10)+(S14-3); (A2-11)+(S1-1); (A2-11)+(S1-7); (A2-11)+(S1-11); (A2-11)+(S2-1); (A2-11)+(S3-1); (A2-11)+(S3-2); (A2-11)+(S3-4); (A2-11)+(S3-7); (A2-11)+(S3-8); (A2-11)+(S3-10); (A2-11)+(S3-11); (A2-11)+(S4-1); (A2-11)+(S4-5); (A2-11)+(S4-6); (A2-11)+(S11-1); (A2-11)+(S11-2); (A2-11)+(S11-3); (A2-11)+(S13-1); (A2-11)+(S13-2); (A2-11)+(S13-3); (A2-11)+(S13-8); (A2-11)+(S14-1); (A2-11)+(S14-2); (A2-11)+(S14-3); (A2-12)+(S1-1); (A2-12)+(S1-7); (A2-12)+(S1-11); (A2-12)+(S2-1); (A2-12)+(S3-1); (A2-12)+(S3-2); (A2-12)+(S3-4); (A2-12)+(S3-7); (A2-12)+(S3-8); (A2-12)+(S3-10); (A2-12)+(S3-11); (A2-12)+(S4-1); (A2-12)+(S4-5); (A2-12)+(S4-6); (A2-12)+(S11-1); (A2-12)+(S11-2); (A2-12)+(S11-3); (A2-12)+(S13-1); (A2-12)+(S13-2); (A2-12)+(S13-3); (A2-12)+(S13-8); (A2-12)+(S14-1); (A2-12)+(S14-2); (A2-12)+(S14-3); (A2-13)+(S1-1); (A2-13)+(S1-7); (A2-13)+(S1-11); (A2-13)+(S2-1); (A2-13)+(S3-1); (A2-13)+(S3-2); (A2-13)+(S3-4); (A2-13)+(S3-7); (A2-13)+(S3-8); (A2-13)+(S3-10); (A2-13)+(S3-11); (A2-13)+(S4-1); (A2-13)+(S4-5); (A2-13)+(S4-6); (A2-13)+(S11-1); (A2-13)+(S11-2); (A2-13)+(S11-3); (A2-13)+(S13-1); (A2-13)+(S13-2); (A2-13)+(S13-3); (A2-13)+(S13-8); (A2-13)+(S14-1); (A2-13)+(S14-2); (A2-13)+(S14-3); (A2-14)+(S1-1); (A2-14)+(S1-7); (A2-14)+(S1-11); (A2-14)+(S2-1); (A2-14)+(S3-1); (A2-14)+(S3-2); (A2-14)+(S3-4); (A2-14)+(S3-7); (A2-14)+(S3-8); (A2-14)+(S3-10); (A2-14)+(S3-11); (A2-14)+(S4-1); (A2-14)+(S4-5); (A2-14)+(S4-6); (A2-14)+(S11-1); (A2-14)+(S11-2); (A2-14)+(S11-3); (A2-14)+(S13-1); (A2-14)+(S13-2); (A2-14)+(S13-3); (A2-14)+(S13-8); (A2-14)+(S14-1); (A2-14)+(S14-2); (A2-14)+(S14-3); (A2-15)+(S1-1); (A2-15)+(S1-7); (A2-15)+(S1-11); (A2-15)+(S2-1); (A2-15)+(S3-1); (A2-15)+(S3-2); (A2-15)+(S3-4); (A2-15)+(S3-7); (A2-15)+(S3-8); (A2-15)+(S3-10); (A2-15)+(S3-11); (A2-15)+(S4-1); (A2-15)+(S4-5); (A2-15)+(S4-6); (A2-15)+(S11-1); (A2-15)+(S11-2); (A2-15)+(S11-3); (A2-15)+(S13-1); (A2-15)+(S13-2); (A2-15)+(S13-3); (A2-15)+(S13-8); (A2-15)+(S14-1); (A2-15)+(S14-2); (A2-15)+(S14-3); (A2-16)+(S1-1); (A2-16)+(S1-7); (A2-16)+(S1-11); (A2-16)+(S2-1); (A2-16)+(S3-1); (A2-16)+(S3-2); (A2-16)+(S3-4); (A2-16)+(S3-7); (A2-16)+(S3-8); (A2-16)+(S3-10); (A2-16)+(S3-11); (A2-16)+(S4-1); (A2-16)+(S4-5); (A2-16)+(S4-6); (A2-16)+(S11-1); (A2-16)+(S11-2); (A2-16)+(S11-3); (A2-16)+(S13-1); (A2-16)+(S13-2); (A2-16)+(S13-3); (A2-16)+(S13-8); (A2-16)+(S14-1); (A2-16)+(S14-2); (A2-16)+(S14-3); (A2-17)+(S1-1); (A2-17)+(S1-7); (A2-17)+(S1-11); (A2-17)+(S2-1); (A2-17)+(S3-1); (A2-17)+(S3-2); (A2-17)+(S3-4); (A2-17)+(S3-7); (A2-17)+(S3-8); (A2-17)+(S3-10); (A2-17)+(S3-11); (A2-17)+(S4-1); (A2-17)+(S4-5); (A2-17)+(S4-6); (A2-17)+(S11-1); (A2-17)+(S11-2); (A2-17)+(S11-3); (A2-17)+(S13-1); (A2-17)+(S13-2); (A2-17)+(S13-3); (A2-17)+(S13-8); (A2-17)+(S14-1); (A2-17)+(S14-2); (A2-17)+(S14-3); (A2-18)+(S1-1); (A2-18)+(S1-7); (A2-18)+(S1-11); (A2-18)+(S2-1); (A2-18)+(S3-1); (A2-18)+(S3-2); (A2-18)+(S3-4); (A2-18)+(S3-7); (A2-18)+(S3-8); (A2-18)+(S3-10); (A2-18)+(S3-11); (A2-18)+(S4-1); (A2-18)+(S4-5); (A2-18)+(S4-6); (A2-18)+(S11-1); (A2-18)+(S11-2); (A2-18)+(S11-3); (A2-18)+(S13-1); (A2-18)+(S13-2); (A2-18)+(S13-3); (A2-18)+(S13-8); (A2-18)+(S14-1); (A2-18)+(S14-2); (A2-18)+(S14-3); (A2-19)+(S1-1); (A2-19)+(S1-7); (A2-19)+(S1-11); (A2-19)+(S2-1); (A2-19)+(S3-1); (A2-19)+(S3-2); (A2-19)+(S3-4); (A2-19)+(S3-7); (A2-19)+(S3-8); (A2-19)+(S3-10); (A2-19)+(S3-11); (A2-19)+(S4-1); (A2-19)+(S4-5); (A2-19)+(S4-6); (A2-19)+(S11-1); (A2-19)+(S11-2); (A2-19)+(S11-3); (A2-19)+(S13-1); (A2-19)+(S13-2); (A2-19)+(S13-3); (A2-19)+(S13-8); (A2-19)+(S14-1); (A2-19)+(S14-2); (A2-19)+(S14-3); (A2-20)+(S1-1); (A2-20)+(S1-7); (A2-20)+(S1-11); (A2-20)+(S2-1); (A2-20)+(S3-1); (A2-20)+(S3-2); (A2-20)+(S3-4); (A2-20)+(S3-7); (A2-20)+(S3-8); (A2-20)+(S3-10); (A2-20)+(S3-11); (A2-20)+(S4-1); (A2-20)+(S4-5); (A2-20)+(S4-6); (A2-20)+(S11-1); (A2-20)+(S11-2); (A2-20)+(S11-3); (A2-20)+(S13-1); (A2-20)+(S13-2); (A2-20)+(S13-3); (A2-20)+(S13-8); (A2-20)+(S14-1); (A2-20)+(S14-2); (A2-20)+(S14-3); (A2-21)+(S1-1); (A2-21)+(S1-7); (A2-21)+(S1-11); (A2-21)+(S2-1); (A2-21)+(S3-1); (A2-21)+(S3-2); (A2-21)+(S3-4); (A2-21)+(S3-7); (A2-21)+(S3-8); (A2-21)+(S3-10); (A2-21)+(S3-11); (A2-21)+(S4-1); (A2-21)+(S4-5); (A2-21)+(S4-6); (A2-21)+(S11-1); (A2-21)+(S11-2); (A2-21)+(S11-3); (A2-21)+(S13-1); (A2-21)+(S13-2); (A2-21)+(S13-3); (A2-21)+(S13-8); (A2-21)+(S14-1); (A2-21)+(S14-2); (A2-21)+(S14-3); (A2-22)+(S1-1); (A2-22)+(S1-7); (A2-22)+(S1-11); (A2-22)+(S2-1); (A2-22)+(S3-1); (A2-22)+(S3-2); (A2-22)+(S3-4); (A2-22)+(S3-7); (A2-22)+(S3-8); (A2-22)+(S3-10); (A2-22)+(S3-11); (A2-22)+(S4-1); (A2-22)+(S4-5); (A2-22)+(S4-6); (A2-22)+(S11-1); (A2-22)+(S11-2); (A2-22)+(S11-3); (A2-22)+(S13-1); (A2-22)+(S13-2); (A2-22)+(S13-3); (A2-22)+(S13-8); (A2-22)+(S14-1); (A2-22)+(S14-2); (A2-22)+(S14-3); (A2-23)+(S1-

1); (A2-23)+(S1-7); (A2-23)+(S1-11); (A2-23)+(S2-1); (A2-23)+(S3-1); (A2-23)+(S3-2); (A2-23)+(S3-4); (A2-23)+(S3-7); (A2-23)+(S3-8); (A2-23)+(S3-10); (A2-23)+(S3-11); (A2-23)+(S4-1); (A2-23)+(S4-5); (A2-23)+(S4-6); (A2-23)+(S11-1); (A2-23)+(S11-2); (A2-23)+(S11-3); (A2-23)+(S13-1); (A2-23)+(S13-2); (A2-23)+(S13-3); (A2-23)+(S13-8); (A2-23)+(S14-1); (A2-23)+(S14-2); (A2-23)+(S14-3); (A2-24)+(S1-1); (A2-24)+(S1-7); (A2-24)+(S1-11); (A2-24)+(S2-1); (A2-24)+(S3-1); (A2-24)+(S3-2); (A2-24)+(S3-4); (A2-24)+(S3-7); (A2-24)+(S3-8); (A2-24)+(S3-10); (A2-24)+(S3-11); (A2-24)+(S4-1); (A2-24)+(S4-5); (A2-24)+(S4-6); (A2-24)+(S11-1); (A2-24)+(S11-2); (A2-24)+(S11-3); (A2-24)+(S13-1); (A2-24)+(S13-2); (A2-24)+(S13-3); (A2-24)+(S13-8); (A2-24)+(S14-1); (A2-24)+(S14-2); (A2-24)+(S14-3); (A2-25)+(S1-1); (A2-25)+(S1-7); (A2-25)+(S1-11); (A2-25)+(S2-1); (A2-25)+(S3-1); (A2-25)+(S3-2); (A2-25)+(S3-4); (A2-25)+(S3-7); (A2-25)+(S3-8); (A2-25)+(S3-10); (A2-25)+(S3-11); (A2-25)+(S4-1); (A2-25)+(S4-5); (A2-25)+(S4-6); (A2-25)+(S11-1); (A2-25)+(S11-2); (A2-25)+(S11-3); (A2-25)+(S13-1); (A2-25)+(S13-2); (A2-25)+(S13-3); (A2-25)+(S13-8); (A2-25)+(S14-1); (A2-25)+(S14-2); (A2-25)+(S14-3); (A2-26)+(S1-1); (A2-26)+(S1-7); (A2-26)+(S1-11); (A2-26)+(S2-1); (A2-26)+(S3-1); (A2-26)+(S3-2); (A2-26)+(S3-4); (A2-26)+(S3-7); (A2-26)+(S3-8); (A2-26)+(S3-10); (A2-26)+(S3-11); (A2-26)+(S4-1); (A2-26)+(S4-5); (A2-26)+(S4-6); (A2-26)+(S11-1); (A2-26)+(S11-2); (A2-26)+(S11-3); (A2-26)+(S13-1); (A2-26)+(S13-2); (A2-26)+(S13-3); (A2-26)+(S13-8); (A2-26)+(S14-1); (A2-26)+(S14-2); (A2-26)+(S14-3); (A2-27)+(S1-1); (A2-27)+(S1-7); (A2-27)+(S1-11); (A2-27)+(S2-1); (A2-27)+(S3-1); (A2-27)+(S3-2); (A2-27)+(S3-4); (A2-27)+(S3-7); (A2-27)+(S3-8); (A2-27)+(S3-10); (A2-27)+(S3-11); (A2-27)+(S4-1); (A2-27)+(S4-5); (A2-27)+(S4-6); (A2-27)+(S11-1); (A2-27)+(S11-2); (A2-27)+(S11-3); (A2-27)+(S13-1); (A2-27)+(S13-2); (A2-27)+(S13-3); (A2-27)+(S13-8); (A2-27)+(S14-1); (A2-27)+(S14-2); (A2-27)+(S14-3); (A2-28)+(S1-1); (A2-28)+(S1-7); (A2-28)+(S1-11); (A2-28)+(S2-1); (A2-28)+(S3-1); (A2-28)+(S3-2); (A2-28)+(S3-4); (A2-28)+(S3-7); (A2-28)+(S3-8); (A2-28)+(S3-10); (A2-28)+(S3-11); (A2-28)+(S4-1); (A2-28)+(S4-5); (A2-28)+(S4-6); (A2-28)+(S11-1); (A2-28)+(S11-2); (A2-28)+(S11-3); (A2-28)+(S13-1); (A2-28)+(S13-2); (A2-28)+(S13-3); (A2-28)+(S13-8); (A2-28)+(S14-1); (A2-28)+(S14-2); (A2-28)+(S14-3); (A2-29)+(S1-1); (A2-29)+(S1-7); (A2-29)+(S1-11); (A2-29)+(S2-1); (A2-29)+(S3-1); (A2-29)+(S3-2); (A2-29)+(S3-4); (A2-29)+(S3-7); (A2-29)+(S3-8); (A2-29)+(S3-10); (A2-29)+(S3-11); (A2-29)+(S4-1); (A2-29)+(S4-5); (A2-29)+(S4-6); (A2-29)+(S11-1); (A2-29)+(S11-2); (A2-29)+(S11-3); (A2-29)+(S13-1); (A2-29)+(S13-2); (A2-29)+(S13-3); (A2-29)+(S13-8); (A2-29)+(S14-1); (A2-29)+(S14-2); (A2-29)+(S14-3); (A2-30)+(S1-1); (A2-30)+(S1-7); (A2-30)+(S1-11); (A2-30)+(S2-1); (A2-30)+(S3-1); (A2-30)+(S3-2); (A2-30)+(S3-4); (A2-30)+(S3-7); (A2-30)+(S3-8); (A2-30)+(S3-10); (A2-30)+(S3-11); (A2-30)+(S4-1); (A2-30)+(S4-5); (A2-30)+(S4-6); (A2-30)+(S11-1); (A2-30)+(S11-2); (A2-30)+(S11-3); (A2-30)+(S13-1); (A2-30)+(S13-2); (A2-30)+(S13-3); (A2-30)+(S13-8); (A2-30)+(S14-1); (A2-30)+(S14-2); (A2-30)+(S14-3); (A2-31)+(S1-1); (A2-31)+(S1-7); (A2-31)+(S1-11); (A2-31)+(S2-1); (A2-31)+(S3-1); (A2-31)+(S3-2); (A2-31)+(S3-4); (A2-31)+(S3-7); (A2-31)+(S3-8); (A2-31)+(S3-10); (A2-31)+(S3-11); (A2-31)+(S4-1); (A2-31)+(S4-5); (A2-31)+(S4-6); (A2-31)+(S11-1); (A2-31)+(S11-2); (A2-31)+(S11-3); (A2-31)+(S13-1); (A2-31)+(S13-2); (A2-31)+(S13-3); (A2-31)+(S13-8); (A2-31)+(S14-1); (A2-31)+(S14-2); (A2-31)+(S14-3); (A2-32)+(S1-1); (A2-32)+(S1-7); (A2-32)+(S1-11); (A2-32)+(S2-1); (A2-32)+(S3-1); (A2-32)+(S3-2); (A2-32)+(S3-4); (A2-32)+(S3-7); (A2-32)+(S3-8); (A2-32)+(S3-10); (A2-32)+(S3-11); (A2-32)+(S4-1); (A2-32)+(S4-5); (A2-32)+(S4-6); (A2-32)+(S11-1); (A2-32)+(S11-2); (A2-32)+(S11-3); (A2-32)+(S13-1); (A2-32)+(S13-2); (A2-32)+(S13-3); (A2-32)+(S13-8); (A2-32)+(S14-1); (A2-32)+(S14-2); (A2-32)+(S14-3); (A2-33)+(S1-1); (A2-33)+(S1-7); (A2-33)+(S1-11); (A2-33)+(S2-1); (A2-33)+(S3-1); (A2-33)+(S3-2); (A2-33)+(S3-4); (A2-33)+(S3-7); (A2-33)+(S3-8); (A2-33)+(S3-10); (A2-33)+(S3-11); (A2-33)+(S4-1); (A2-33)+(S4-5); (A2-33)+(S4-6); (A2-33)+(S11-1); (A2-33)+(S11-2); (A2-33)+(S11-3); (A2-33)+(S13-1); (A2-33)+(S13-2); (A2-33)+(S13-3); (A2-33)+(S13-8); (A2-33)+(S14-1); (A2-33)+(S14-2); (A2-33)+(S14-3); (A2-34)+(S1-1); (A2-34)+(S1-7); (A2-34)+(S1-11); (A2-34)+(S2-1); (A2-34)+(S3-1); (A2-34)+(S3-2); (A2-34)+(S3-4); (A2-34)+(S3-7); (A2-34)+(S3-8); (A2-34)+(S3-10); (A2-34)+(S3-11); (A2-34)+(S4-1); (A2-34)+(S4-5); (A2-34)+(S4-6); (A2-34)+(S11-1); (A2-34)+(S11-2); (A2-34)+(S11-3); (A2-34)+(S13-1); (A2-34)+(S13-2); (A2-34)+(S13-3); (A2-34)+(S13-8); (A2-34)+(S14-1); (A2-34)+(S14-2); (A2-34)+(S14-3); (A2-35)+(S1-1); (A2-35)+(S1-7); (A2-35)+(S1-11); (A2-35)+(S2-1); (A2-35)+(S3-1); (A2-35)+(S3-2); (A2-35)+(S3-4); (A2-35)+(S3-7); (A2-35)+(S3-8); (A2-35)+(S3-10); (A2-35)+(S3-11); (A2-35)+(S4-1); (A2-35)+(S4-5); (A2-35)+(S4-6); (A2-35)+(S11-1); (A2-35)+(S11-2); (A2-35)+(S11-3); (A2-35)+(S13-1); (A2-35)+(S13-2); (A2-35)+(S13-3); (A2-35)+(S13-8); (A2-35)+(S14-1); (A2-35)+(S14-2); (A2-35)+(S14-3); (A2-36)+(S1-1); (A2-36)+(S1-7); (A2-36)+(S1-11); (A2-36)+(S2-1); (A2-36)+(S3-1); (A2-36)+(S3-2); (A2-36)+(S3-4); (A2-36)+(S3-7); (A2-36)+(S3-8); (A2-36)+(S3-10); (A2-36)+(S3-11); (A2-36)+(S4-1); (A2-36)+(S4-5); (A2-36)+(S4-6); (A2-36)+(S11-1); (A2-36)+(S11-2); (A2-36)+(S11-3); (A2-36)+(S13-1); (A2-36)+(S13-2); (A2-36)+(S13-3); (A2-36)+(S13-8); (A2-36)+(S14-1); (A2-36)+(S14-2); (A2-36)+(S14-3);

In the context of the present invention, preference is given especially to combinations of the compounds of the general formula (I) with the following safeners: mefenpyr-diethyl, fenchlorazole, isoxadifen-ethyl, cloquintocet-mexyl, dichlormid, 3-dichloroacetyl-2,2,5-trimethyl-1,3-oxazolidine, benoxacor, 3-dichloroacetyl-1-oxa-3-azaspiro[4,5]decane, 1-dichloroacetylazepane, furilazole, ((R)-3-dichloroacetyl-5-(2-fury))-2,2-dimethyloxazolidine), cyprosulfamide, N-isopropyl-4-sulfamoylbenzamide-1-(2-methoxyphenyl) ethanone, 1-[4-(N-2-methoxybenzoylsulfamoyl)phenyl]-3-methylurea, oxabetrinil, fluxofenim, cyometrinil, 1,8-naphthalenedicarboxylic anhydride, fenclorim, flurazole, dietholate, dimepiperate, daimuron and cumyluron.

In the context of the present invention, very particular preference is given to combinations of the compounds of the general formula (I) with the following safeners: daimuron, benoxacor, furilazole, fluxofenim, fenchlorazole (ethyl ester), mefenpyr-diethyl, cloquintocet-mexyl, isoxadifen-ethyl, cyprosulfamide, flurazole, oxabetrinil, dichlormid and dietholate.

In the context of the present invention, preference is even more preferably given to combinations of the compounds of the general formula (I) with the following safeners: mefenpyr-diethyl, isoxadifen-ethyl, cyprosulfamide, fenchlorazole ethyl ester, benoxacor, cloquintocet-mexyl, fluxofenim and furilazole.

Preference is given to herbicide-safener combinations comprising (A) a herbicidally active amount of one or more compounds of the formula (I) or salts thereof and (B) an antidotically active amount of one or more safeners.

A "herbicidally active amount" in the context of the invention means an amount of one or more herbicides suitable for adversely affecting plant growth. An "antidotically active amount" in the context of the invention means an amount of one or more safeners suitable for reducing the phytotoxic effect of active ingredients of crop protection compositions (for example of herbicides) on crop plants.

The safeners (B) are suitable for reduction of phytotoxic effects which can occur when herbicides of the general formula (I) are used in crops of useful plants, without significantly impairing the efficacy of these active herbicidal ingredients against harmful plants. As a result of this, it is possible to extend the field of use of conventional crop protection compositions quite considerably, for example to crops in which use of the herbicides has been possible to date only to a limited degree, if at all.

According to the indication and active herbicidal ingredient used, the application rates of the safeners required may vary within wide limits and are generally in the range from 0.001 to 5 kg, preferably 0.005 to 2.5 kg and particularly 0.05 to 0.5 kg of active ingredient per hectare.

The active herbicidal ingredients of the general formula (I) (A) and the safeners (B) can be deployed together (for example as a ready-made formulation or by the tank-mix method) or successively in any sequence, for example by application by spraying, watering and sprinkling, or by granule scattering. The weight ratio of herbicide of the general formula (I) (A):safener (B) may vary within wide limits and is preferably in the range from 1:10000 to 10000:1, especially from 1:1000 to 1000:1 and very particularly from 1:20 to 20:1. The amounts of herbicides (A) the general formula (I) and safener (B) which are optimal in each case depend on the type of herbicide used and the safener used and on the nature and development stage of the plant stock to be treated, and can be determined in each individual case by simple, routine preliminary tests.

According to their properties, the safeners (B) present in the inventive herbicide-safener combination can be used for pretreatment of the seed of the crop plant (for example for dressing of the seed) or introduced into the seed furrows prior to sowing or employed together with the herbicide prior to or after emergence of the plants. Pre-emergence treatment includes both the treatment of the area under cultivation (including any water present in the area under cultivation, for example in the case of applications to rice) prior to sowing and the treatment of the area under cultivation in which seeds have been sown but which is not yet covered by growing plants. Preference is given to application together with the herbicide. For this purpose, it is possible to use tank-mixes or ready-made formulations.

In a preferred embodiment, the seed (for example grains, seeds or vegetative propagation organs such as tubers or budded parts of shoots) or seedlings are pretreated with the safeners (B), optionally in combination with other active agrochemical ingredients. For pretreatment of the seed, the active ingredients can be applied to the seed, for example by dressing, or the active ingredients and the seed can be added to water or other solvents, and the active ingredients can be taken up, for example, by adsorption or diffusion in a dipping process or by swelling or pre-germination. For pretreatment of seedlings, the young plants can be contacted with the safeners, optionally in combination with other active agrochemical ingredients, for example by spraying, dipping or watering, and then transplanted and optionally aftertreated with the herbicides (A).

The seed or seedlings can be treated with the safeners (B) alone or together with other active agrochemical ingredients—such as fungicides, insecticides or plant fortifiers, fertilizers or swelling and germination accelerators. After the pretreatment application, the safeners may subsequently be applied once again before, after or together with one or more herbicides of the formula (I), possibly also in combination with other known herbicides. The pretreatment of the seed or seedlings can achieve improved long-term action of the safeners.

The present invention thus further provides a method for controlling unwanted plants in plant crops, which is characterized in that components (A) and (B) of the inventive herbicide-safener combination are deployed, for example separately or together, on the plants (for example harmful plants such as mono- or dicotyledonous weeds or unwanted crop plants), the seed (for example grains, seeds or vegetative propagation organs such as tubers or budded parts of shoots) or the area on which the plants grow (for example the area under cultivation). It is possible here to apply one or more safeners (B), preferably one or more compounds, especially one compound, of groups (S1) to (S15) before, after or simultaneously with the herbicide(s) of the general formula (I) (A) to the plants, the seed or the area on which the plants grow (for example the area under cultivation). In a preferred embodiment, the safeners (B) are used for seed treatment.

Unwanted plants are understood to mean all plants which grow at sites where they are unwanted. These may, for example, be harmful plants (for example monocotyledonous or dicotyledonous weeds or unwanted crop plants), including, for example, those which are resistant to certain active herbicidal ingredients, such as glyphosate, atrazine, glufosinate or imidazolinone herbicides.

Monocotyledonous weeds are classified, for example in the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera*. Dicotyledonous weeds are classified, for example, in the genera Sinapis, *Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia*.

Preferably, in the method according to the invention, an effective amount of components (A) and (B) for control of harmful plants is applied in plant crops, for example in economically important farm crops, e.g. monocotyledonous farm crops such as cereals (e.g. wheat, barley, rye, oats), rice, corn, millet/sorghum, or dicotyledonous farm crops such as sugar beet, oilseed rape, cotton, sunflower and legumes, for example of the genera *Glycine* (e.g. *Glycine max.* such as non-transgenic *Glycine max.* (e.g. conventional varieties such as STS varieties) or transgenic *Glycine max.* (e.g. RR soya or LL soya) and crosses thereof), *Phaseolus, Pisum, Vicia* and *Arachis*, or vegetable crops from various botanic groups, such as potato, leek, cabbage, carrot, tomato, onion, and permanent crops and plantation crops such as pome fruit and stone fruit, berries, grapes, hevea, bananas, sugar cane, coffee, tea, citrus, nut plantations, lawns, palm crops and forestry crops.

The invention also provides for the use of the inventive herbicide-safener combinations for controlling unwanted vegetation, preferably in plant crops.

The inventive herbicide-safener combinations can be produced by known processes, for example as mixed formulations of the individual components, optionally with further active ingredients, additives and/or customary formulation auxiliaries, which are then applied in a customary manner diluted with water, or as what are called tank-mixes by co-dilution of the separately formulated or partially separately formulated individual components with water. Likewise possible is the application at different times (split application) of the separately formulated or partially separately formulated individual components. It is also possible, for example, to apply the individual components or the herbicide-safener combinations in several portions (sequential application), for example pre-emergence applications followed by post-emergence applications, or early post-emergence applications followed by post-emergence applications at an intermediate or late stage. Preference is given to the joint or immediately successive application of the active ingredients in the respective combination.

The inventive herbicide-safener combination can also be used for control of harmful plants in crops of genetically modified plants which are known or are yet to be developed.

In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material. Further particular properties may be tolerance or resistance to abiotic stress factors, for example heat, cold, drought, salinity and ultraviolet radiation.

Preference is given to the use of the inventive herbicide-safener combinations or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

genetic modifications of crop plants for the purpose of modifying the starch synthesized in the plants (for example WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which cause an increased disease resistance (EPA 309862, EPA0464461), genetically modified plants with reduced photorespiration, which have higher yields and higher stress tolerance (EPA 0305398), transgenic crop plants which produce pharmaceutically or diagnostically important proteins ("molecular pharming"), transgenic crop plants which are notable for higher yields or better quality, transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.), Gene Transfer to Plants, Springer Lab Manual (1995), Springer Verlag Berlin, Heidelberg or Christou, "Trends in Plant Science" 1 (1996) 423-431.

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim, 2nd edition, 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product.

For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, in order to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants can be plants of any desired plant species, i.e. not only monocotyledonous, but also dicotyledonous, plants.

Thus, it is possible to obtain transgenic plants whose properties are altered by overexpression, suppression or inhibition of homologous (=natural) genes or gene sequences, or expression of heterologous (=foreign) genes or gene sequences.

Preferably, the inventive herbicide-safener combinations can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the inventive herbicide-safener combinations in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive herbicide-safener combinations for control of harmful plants in transgenic crop plants.

Preference is given to the use of the inventive combinations in economically important transgenic crops of useful plants and ornamentals, for example of cereals (e.g. wheat, barley, rye, oats), millet/sorghum, rice, manioc and corn, or else crops of sugar beet, cotton, soybean, oilseed rape, potato, tomato, peas and other vegetable crops.

The invention therefore also provides for the use of the inventive herbicide-safener combinations for control of harmful plants in transgenic crop plants or crop plants having tolerance through selective breeding.

The herbicides (A) and the safeners (B) can be converted together or separately to customary formulations, for example for application by spraying, watering, sprinkling and seed dressing, such as solutions, emulsions, suspensions, powders, foams, pastes, granules, aerosols, active ingredient-impregnated natural and synthetic substances, microencapsulations in polymeric substances. The formulations may comprise the customary auxiliaries and additives.

These formulations are produced in a known manner, for example by mixing the active ingredients with extenders, i.e. liquid solvents, pressurized liquefied gases and/or solid carriers, optionally with use of surfactants, i.e. emulsifiers and/or dispersants and/or foam generators.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and the ethers and esters thereof, ketones such as acetone, methyl ethyl ketone, methyl isobutyl ketone or cyclohexanone, strongly polar solvents such as dimethylformamide or dimethyl sulfoxide, and water.

Useful solid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and silicates; useful solid carriers for granules include: for example crushed and fractionated natural rocks, such as calcite, marble, pumice, sepiolite, dolomite and synthetic granules of inorganic and organic flours, and granules of organic material, such as sawdust, coconut shells, corn cobs and tobacco stalks; useful emulsifiers and/or foam generators include: for example nonionic and anionic emulsifiers, such as polyoxyethylene fatty acid esters, polyoxyethylene fatty alcohol ethers, e.g. alkylaryl polyglycol ethers, alkylsulfonates, alkylsulfates, arylsulfonates and protein hydrolyzates; useful dispersants include: for example lignosulfite waste liquors and methylcellulose.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

The formulations contain generally between 0.1 and 95 percent by weight of active ingredient, preferably between 0.5 and 90% by weight.

The herbicides (A) and the safeners (B) can also be used as such or in formulations thereof in a mixture with other active agrochemical ingredients, such as known herbicides, for controlling unwanted vegetation, for example for controlling weeds or for controlling unwanted crop plants, possible examples being ready-made formulations or tank-mixes.

Also possible are mixtures with other known active ingredients such as fungicides, insecticides, acaricides, nematicides, bird antifeedants, plant nutrients and soil improvers, and likewise with additives and formulation auxiliaries customary in plant protection.

The herbicides (A) and the safeners (B) can be used as such, in the form of formulations thereof or in the use forms prepared therefrom by further dilution, such as ready-to-use solutions, suspensions, emulsions, powders, pastes and granules.

Application is typically accomplished, for example, by watering, sprinking, spraying, broadcasting.

The active ingredients can be deployed on the plants, plant parts, seed or area under cultivation (farmland), preferably on the seed or the green plants and plant parts, and optionally additionally to the farmland. One means of application is the co-deployment of the active ingredients in the form of tank-mixes, by mixing the optimally formulated concentrated formulations of the individual active ingredients together in the tank with water and deploying the spray liquor obtained.

A co-formulation of the inventive combination of active ingredients (A) and (B) has the advantage of easier applicability, because the amounts of the components can already be set in the optimal ratio with respect to one another. Moreover, the auxiliaries in the formulation can be optimized to one another.

Combination partners usable for the inventive herbicide-safener combination in mixed formulations or in a tank-mix are, for example, known, preferably herbicidal, active ingredients based on inhibition of, for example, acetolactate synthase, acetyl coenzyme A carboxylase, PS I, PS II, HPPD, phytoene desaturase, protoporphyrinogen oxidase, glutamine synthetase, cellulose biosynthesis, 5-enolpyruvylshikimate-3-phosphate synthetase. Such compounds and also other usable compounds, some with an unknown or different mechanism of action, are described, for example, in Weed Research 26, 441-445 (1986), or in the handbook "The Pesticide Manual", 12th edition 2000, or 13th edition 2003 or 14th edition 2006/2007, or in the corresponding "e-Pesticide Manual", Version 5.0 (2008-10), each published by the British Crop Protection Council, (also referred to hereinafter as "PM"), and literature cited therein. Lists of common names are also available in "The Compendium of Pesticide Common Names" on the Internet. Examples of herbicides known from the literature which can be combined with the inventive herbicide-safener combinations include the active ingredients which follow (N.B.: The compounds are designated either by the common name according to the International Organization for Standardization (ISO) or by the chemical name, in some cases together with a standard code number, and always encompass all use forms, such as acids, salts, esters and isomers, such as stereoisomers and optical isomers. In this case, one or else, in some cases, more than one application form is mentioned.):

2,4-D, acetochlor, acifluorfen, acifluorfen-sodium, aclonifen, alachlor, alloxydim, alloxydim-sodium, ametryn, amicarbazone, amidosulfuron, aminopyralid, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bifenox, bilanafos, bispyribac-sodium, bromacil, bromobutide, bromofenoxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlortoluron, chlorsulfuron, cinidon-ethyl, cinmethylin, cinosulfuron, clefoxydim, clethodim, clodinafop-propargyl, clomazone, clomeprop, clopyralid, cloransulam-methyl, cumyluron, cyanazine, cyclosulfamuron, cycloxydim, cyhalofop-butyl, desmedipham, dicamba, dichlobenil, dichlorprop, dichlorprop-P, diclofop-methyl, diclosulam, difenzoquat, diflufenican, diflufenzopyr, dikegulac-sodium, dimefuron, dimepiperate, dimethachlor, dimethametryn, dimethenamid, Triaziflam, diquat-dibromide, dithiopyr, diuron, dymron, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, flamprop-M-isopropyl, flamprop-M-methyl, flazasulfuron, florasulam, fluazifop, fluazifop-butyl, fluazifop-P-butyl, fluazolate, flucarbazone-sodium, flucetosulfuron, fluchloralin, flufenacet, flufenpyr, flumetsulam, flumiclorac-pentyl, flumioxazin, fluometuron, fluorchloridone, fluorglycofen-ethyl, flupoxam, flupyrsulfuron-methyl-sodium, fluridone, fluoroxypyr, fluoroxypyr-butoxypropyl, fluoroxypyr-meptyl, flurprimidol, flurtamone, fluthiacet-methyl, fomesafen, foramsulfuron, glufosinate, glufosinate-P, glufosinate-ammonium, glufosinate-P-ammonium, glufosinate-P-sodium, glyphosate, halosulfuron-methyl, haloxyfop, haloxyfop-ethoxyethyl, haloxyfop-methyl, haloxyfop-P-methyl, hexazinone, imazamethabenz-methyl, imazamox, imazapic, imazapyr, imazaquin, imazethapyr, imazosulfuron, indanofan, indaziflam, iodosulfuron-methyl-sodium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, methabenzthiazuron, methiozolin, methyldymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxsulam, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyrisulfuron, propyzamide, prosulfocarb, prosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenylchlor, thiazopyr, thifensulfuron-methyl, thiobencarb, tiocarbazil, tralkoxydim, triallate, triasulfuron, tribenuron-methyl, triclopyr, tridiphane, trifloxysulfuron, trifluralin, triflusulfuron-methyl and tritosulfuron.

Further possible mixing partners are pyroxasulfone, pyroxsulam, orthosulfamuron, pyrimisulfan, prohexadione-calcium, bencarbazone, SYN-523, IDH-100, SYP-249, monosulfuron, ipfencarbazone (HOK-201), pyribambenz-isopropyl, tefuryltrione, bencarbazone, tembotrione, pyrasulfotole and thiencarbazone-methyl.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

BIOLOGICAL EXAMPLES

Post-Emergence Herbicide Action and Safener Action

Seeds or rhizome pieces of mono- and dicotyledonous harmful plants and of crop plants are placed in sandy loam in peat pots, covered with soil and grown in a greenhouse under good growth conditions. Alternatively, harmful plants which occur in paddy rice cultivation are cultivated in pots containing water to a depth of 2 cm above the soil surface. Ten to twenty days after sowing, the test plants are treated at the one-to three-leaf stage. The inventive herbicide-safener compositions formulated as water-soluble powders or suspensions and, in parallel tests, the correspondingly formulated individual active ingredients are sprayed onto the green plant parts in various dosages with a water application rate of 300 l/ha (converted) and, after the test plants have been left to stand in the greenhouse under optimal growth conditions for 2-3 weeks, the effect of the preparations is assessed visually compared to untreated controls. In the case of rice or in the case of harmful plants which occur in rice cultivation, the active ingredients are also added directly to the irrigation water (application in analogy to what is called granule application) or sprayed onto plants and into the irrigation water.

The experiments show that the use of the inventive herbicide-safener compositions significantly reduces the damage to crop plants such as corn, rice, wheat or barley compared to the use of the individual herbicides without safener—i.e. by 30% up to 100%. At the same time, the effect of the herbicide on economically important harmful plants is not significantly impaired, if at all, and so good post-emergence herbicidal action against a broad spectrum of weed grasses and broad-leaved weeds can be achieved.

For example, in barley, for the herbicide-safener compositions (A1-85)+(S1-1), (A1-85)+(S1-11), (A1-85)+(S4-1), (A1-85)+(S2-1), (A1-85)+(S3-4), (A1-85)+(S11-2), (A1-62)+(S1-1), (A1-62)+(S1-11), (A1-62)+(S4-1), (A1-62)+(S2-1), (A1-62)+(S3-4), (A1-62)+(S3-10) and (A1-62)+(S11-2), good compatibility was achieved with respect to the crop plants with simultaneously good post-emergence herbicidal action against a broad spectrum of harmful plants.

In wheat, for example, for the herbicide-safener compositions (A1-85)+(S1-1), (A1-85)+(S1-11), (A1-85)+(S4-1), (A1-85)+(S2-1), (A1-85)+(S3-4), (A1-85)+(S3-10), (A1-85)+(S11-2), (A1-62)+(S1-11), (A1-62)+(S4-1), (A1-62)+(S2-1), (A1-62)+(S3-4), (A1-85)+(S3-10) and (A1-62)+(S11-2), good compatibility was achieved with respect to the crop plants with simultaneously good post-emergence herbicidal action against a broad spectrum of harmful plants.

In corn, for example, for the herbicide-safener compositions (A1-85)+(S1-1), (A1-85)+(S1-11), (A1-85)+(S2-1) and (A1-85)+(S3-4) good compatibility was achieved with respect to the crop plants with simultaneously good post-emergence herbicidal action against a broad spectrum of harmful plants.

Pre-Emergence Herbicide Action and Safener Action

Seeds or rhizome pieces of mono- and dicotyledonous weed plants and crop plants were placed in sandy loam in peat pots and covered with soil. The inventive herbicide-safener compositions formulated as water-soluble powders or suspensions and, in parallel tests, the correspondingly formulated individual active ingredients were then applied to the surface of the covering soil in various dosages at a water application rate of 600 to 800 l/ha (converted). After the treatment, the pots were placed in a greenhouse and kept under good growth conditions for the weeds and the crop plants. The plant or emergence damage was scored visually after the emergence of the test plants, after a test time of 2 to 4 weeks, in comparison to untreated controls.

In corn, for example, for the herbicide-safener compositions (A1-85)+(S1-11), (A1-85)+(S4-1), (A1-85)+(S2-1), (A1-85)+(S3-4), (A1-85)+(S3-10), (A1-85)+(S11-2), (A1-85)+(S1-7), (A1-62)+(S1-1), (A1-62)+(S4-1), (A1-62)+(S2-1), (A1-62)+(S3-4), (A1-85)+(S3-10) (A1-62)+(S11-2) and (A1-62)+(S1-7), good compatibility was achieved with respect to the crop plants with simultaneously good pre-emergence herbicidal action against a broad spectrum of harmful plants.

Seed Treatment

Seed grains of crop plants were mixed and shaken well in bottles with the safeners formulated as suspension or emulsion concentrates and water, such that the seed grains were coated homogeneously with the formulation of the respective safener. The seed grains or the plants after emergence were then treated with herbicides by the pre-emergence or post-emergence method. Numerous inventive herbicide-safener compositions showed good compatibility with respect to the crop plants with simultaneously good herbicidal action against a broad spectrum of harmful plants.

The invention claimed is:

1. A herbicide-safener composition comprising:
(A) at least one compound of formula (I) and/or a salt thereof

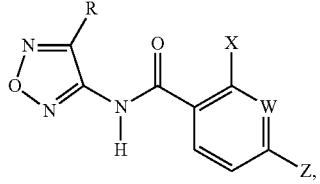

(I)

in which
W is N,
R is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, $(C_2-C_6)$-haloalkenyl, $(C_2-C_6)$-alkynyl, $(C_2-C_6)$-alkynyloxy, $(C_2-C_6)$-haloalkynyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, or methoxymethyl, or
is heteroaryl, heterocyclyl or phenyl, each being substituted by s radicals selected from the group consisting of methyl, ethyl, methoxy, trifluoromethyl and halogen,
X and Z are each independently nitro, halogen, cyano, formyl, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR^1R^2$, or $P(O)(OR^5)_2$, or
is heteroaryl, heterocyclyl or phenyl each substituted by s radicals selected from the group consisting of methyl, ethyl, methoxy, nitro, trifluoromethyl and halogen,
$R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl or phenyl-$(C_1-C_6)$-alkyl, where the 12 latter radicals are substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^3$, $NR^3COR^3$, $CO_2R^3$, $COSR^3$, $CON(R^3)_2$ and $(C_1-C_4)$-alkoxy-$(C_2-C_6)$-alkoxycarbonyl,
$R^2$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, phenyl or phenyl-$(C_1-C_6)$-alkyl, each being substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^3$, $NR^3COR^3$, $CO_2R^3$, $COSR^3$, $CON(R^3)_2$ and $(C_1-C_4)$-alkoxy-$(C_2-C_6)$-alkoxycarbonyl,
$R^3$ is hydrogen, $(C_1-C_6)$-alkyl, $(C_2-C_6)$-alkenyl or $(C_2-C_6)$-alkynyl,
$R^4$ is $(C_1-C_6)$-alkyl, $(C_2-C_6)$-alkenyl or $(C_2-C_6)$-alkynyl,
$R^5$ is methyl or ethyl,
n is 0, 1 or 2, and
s is 0, 1, 2 or 3,
and
(B) at least one safener.

2. The herbicide-safener composition as claimed in claim 1, in which
W is N,
R is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, acetylamino, benzoylamino, methoxycarbonyl, ethoxycarbonyl, benzoyl, methylcarbonyl, piperidinylcarbonyl, trifluoromethylcarbonyl, halogen, amino, aminocarbonyl, methylaminocarbonyl, dimethylaminocarbonyl, or methoxymethyl, X and Z are each independently nitro, halogen, cyano, $(C_1-C_6)$-alkyl, $(C_1-C_6)$-haloalkyl, $(C_3-C_6)$-cycloalkyl, $OR^1$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$ or 1,2,4-triazol-1-yl, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, phenyl or phenyl-$(C_1-C_6)$-alkyl, where the seven latter radicals are substituted by s radicals selected from the group consisting of halogen and $OR^3$, $R^2$ is $(C_1-C_6)$-alkyl, $(C_3-C_6)$-cycloalkyl or $(C_3-C_6)$-cycloalkyl-$(C_1-C_6)$-alkyl, each being substituted by s radicals selected from the group consisting of halogen and $OR^3$, $R^3$ is hydrogen or $(C_1-C_6)$-alkyl, n is 0, 1 or 2, and s is 0, 1, 2 or 3.

3. The herbicide-safener composition as claimed in claim 1, in which

W is N,

R is amino, cyclopropyl, isopropyl, t-butyl, methyl, ethyl, methoxy, bromine or chlorine, X is chlorine, methoxymethyl or methyl, and Z is trifluoromethyl.

4. The herbicide-safener composition as claimed in claim 1, comprising at least one safener selected from the group consisting of mefenpyr-diethyl, fenchlorazole, isoxadifen-ethyl, cloquintocet-mexyl, dichlormid, 3-dichloroacetyl-2,2,5-trimethyl-1,3-oxazolidine, benoxacor, 3-dichloroacetyl-1-oxa-3-azaspiro[4.5]decane, 1-dichloroacetylazepane, furilazole, ((R)-3-dichloroacetyl-5-(2-furyl)-2,2-dimethyloxazolidine), cyprosulfamide, N-isopropyl-4-sulfamoylbenzamide, 1-(2-methoxyphenyl)ethanone, 1-[4-(N-2-methoxybenzoylsulfamoyl)phenyl]-3-methylurea, oxabetrinil, fluxofenim, cyometrinil, 1,8-naphthalenedicarboxylic anhydride, fenclorim, flurazole, dietholate, dimepiperate, daimuron and cumyluron.

5. The herbicide-safener composition as claimed in claim 4, comprising at least one safener selected from the group consisting of daimuron, benoxacor, furilazole, fluxofenim, fenchlorazole (ethyl ester), mefenpyr-diethyl, cloquintocet-mexyl, isoxadifen-ethyl, cyprosulfamide, flurazole, oxabetrinil, dichlormid and dietholate.

6. The herbicide-safener composition as claimed in claim 5, comprising at least one compound of formula (I) and/or salt thereof and at least one safener selected from the group consisting of mefenpyr-diethyl, isoxadifen-ethyl, cyprosulfamide, fenchlorazole ethyl ester, benoxacor, cloquintocet-mexyl, fluxofenim and furilazole.

7. A method for controlling a harmful plant in a crop comprising applying a herbicidally active amount of a composition as claimed in of claim 1 to said harmful plant, a plant part, a plant seed and/or an area on which a plant grows.

8. The method as claimed in claim 7, wherein the crop is selected from the group consisting of sugarcane, corn, wheat, rye, barley, oats, rice, sorghum, cotton and soya.

9. The method as claimed in claim 7, wherein the crop has been genetically modified.

* * * * *